US009280884B1

(12) United States Patent
Schultz et al.

(10) Patent No.: US 9,280,884 B1
(45) Date of Patent: Mar. 8, 2016

(54) ENVIRONMENTAL SENSOR DEVICE WITH ALARMS

(71) Applicant: Oberon, Inc., State College, PA (US)

(72) Inventors: Richard Douglas Schultz, Fernandina Beach, FL (US); David Glenn DeGroote, State College, PA (US); Travis James Weaver, PA Furnace, PA (US); Scott Thompson, State College, PA (US)

(73) Assignee: Oberon, Inc., State College, PA (US)

( * ) Notice: Subject to any disclaimer, the term of this patent is extended or adjusted under 35 U.S.C. 154(b) by 0 days.

(21) Appl. No.: 14/476,138

(22) Filed: Sep. 3, 2014

(51) Int. Cl.
*G08B 19/00* (2006.01)
*G01N 33/00* (2006.01)
*F24F 11/00* (2006.01)
*G01N 1/22* (2006.01)

(52) U.S. Cl.
CPC ............ *G08B 19/00* (2013.01); *F24F 11/0017* (2013.01); *G01N 1/2273* (2013.01); *G01N 33/0063* (2013.01); *A61B 2560/0242* (2013.01)

(58) Field of Classification Search
CPC .............. G01N 1/2273; G01N 33/0063; F24F 11/0017; A61B 2560/0242
USPC ................... 340/522, 603; 73/28.01; 454/187
See application file for complete search history.

(56) References Cited

U.S. PATENT DOCUMENTS

| | | | | |
|---|---|---|---|---|
| 6,473,668 | B2* | 10/2002 | Abuzeid | F24F 11/006 |
| | | | | 198/810.01 |
| 6,888,453 | B2* | 5/2005 | Lutz | G08C 19/00 |
| | | | | 340/506 |
| 8,147,302 | B2* | 4/2012 | Desrochers | F24F 3/044 |
| | | | | 340/632 |
| 9,109,981 | B2* | 8/2015 | Sharp | G01N 1/2273 |
| 2013/0324026 | A1* | 12/2013 | Fiorita, Jr. | F24F 3/161 |
| | | | | 454/187 |
| 2014/0262134 | A1* | 9/2014 | Arensmeier | F24F 11/02 |
| | | | | 137/56 |

* cited by examiner

*Primary Examiner* — John A Tweel, Jr.
(74) *Attorney, Agent, or Firm* — David Grossman

(57) ABSTRACT

An environmental sensor device with alarms comprises a data bus, a multitude of sensors, at least one processing unit, a communications interface, and memory. The multitude of sensors may include particle counter(s), pressure sensor(s) and/or the like. The memory is configured to hold data and machine executable instructions. The machine executable instructions are configured to cause at least one processing unit to: collect sensor data from at least one of the multitude of sensors, generate processed sensor data from the sensor data, and set alarm(s) based, at least in part on processed sensor data. The communications interface is configured to communicate the report to at least one external device.

20 Claims, 10 Drawing Sheets

Threshold Setup Interface 721

Environmental Monitor

[System Options] [Overview] [Admin] [Options] [Log Out]

Default Settings

| Sensor | N/A | Alarm | Threshold |
|---|---|---|---|
| Room Pressure: | ☐ | ☐ | 5.0 Pa |
| Relative Humidity: | ☐ | ☑ | 60 High  30 Low % |
| Sound: | ☐ | ☑ | 80 dB SPL |
| Light: | ☐ | ☐ | 2,000 High  200 Low Lux |
| Air Quality: | ☐ | ☑ | 1,000 R-T  1,000 STEL  1,000 TWA ppm |
| ISO / Class: | ☐ | ☑ | 1,000 R-T  1,000 STEL  1,000 TWA ppm |
| 0.5 µm: | ☐ | ☐ | 3520000.000 Particles/m³ (2 mins) |
| Particles  1 µm: | ☐ | ☐ | 832000.000 Particles/m³ (2 mins) |
| 5 µm: | ☐ | ☐ | 28666.667 Particles/m³ (2 mins) |
| 10 µm: | ☐ | ☐ | 6666.667 Particles/m³ (4 mins) |

Update all units: ☐  [Update Thresholds] [Default Thresholds]

FIG. 7

| ISO 14644-1 Cleanroom Standard, Maximum Particles/m^3 | | | | | | | |
|---|---|---|---|---|---|---|---|
| Class | ≥0.1um | ≥0.2um | ≥0.3um | ≥0.5um | ≥1um | ≥5um | FED STD 209E Equivalent |
| ISO 1 | 10 | 2.37 | 1.02 | 0.35 | 0.083 | 0.0029 | N/A |
| ISO 2 | 100 | 23.7 | 10.2 | 3.5 | 0.83 | 0.029 | N/A |
| ISO 3 | 1,000 | 237 | 102 | 35 | 8.3 | 0.29 | Class 1 |
| ISO 4 | 10,000 | 2,370 | 1,020 | 352 | 83 | 2.9 | Class 10 |
| ISO 5 | 100,000 | 23,700 | 10,200 | 3,520 | 832 | 29 | Class 100 |
| ISO 6 | 1E6 | 237,000 | 102,000 | 35,200 | 8,320 | 293 | Class 1,000 |
| ISO 7 | 10E6 | 2.37E6 | 1.02E6 | 352,000 | 83,200 | 2,930 | Class 10,000 |
| ISO 8 | 100E6 | 23.7E6 | 10.2E6 | 3.52E6 | 832,000 | 29,300 | Class 100,000 |
| ISO 9 | 1E9 | 237E6 | 102E6 | 35.2E6 | 8.32E6 | 293,000 | N/A, Urban Air |

FIG. 8A

| IC Sentinel® ISO Class Limits, Maximum Particles/m^3 | | | | |
|---|---|---|---|---|
| ISO/FED STD Class | ≥0.5um | ≥1um | ≥5um | ≥10um |
| ISO 3/Class 1 | 35 | 8.3 | 0.29 | 0.07 |
| ISO 4/Class 10 | 352 | 83 | 2.9 | 0.69 |
| ISO 5/Class 100 | 3,520 | 832 | 29 | 6.93 |
| ISO 6/Class 1,000 | 35,200 | 8,320 | 293 | 69.3 |
| ISO 7/Class 10,000 | 352,000 | 83,200 | 2,930 | 693 |
| ISO 8/Class 100,000 | 3,520,000 | 832,000 | 29,300 | 6,925 |
| ISO 9/Urban Air | 35,200,000 | 8,320,000 | 293,000 | 69,255 |

FIG. 8B

|  | Protective Environment(PE) Positive Pressure | Airborne Infection Isolation (AII) Negative pressure |
|---|---|---|
| Pressure Differentials | > + 2.5 Pa (Pascal) (0.01" Positive water gauge) | > - 2.5 Pa (Pascal) (0.01" Negative water gauge) |
| Air Changes per Hour (ACH) | ≥ 12 | ≥ 12 (for renovation or new construction) |
| Filtration Efficiency | Supply: 99.97%@ 0.3um DOP[1] Return: none required[2] | Supply: 90% dust spot test Return: 99.97%@0.3um DOP[1,3] |
| Room Air Flow Direction | Out to the adjacent area | In to the room |
| Clean to Dirty air flow in room | Away from high risk /immunosuppressed patient | Towards the patient (Airborne disease patient ) |
| Ideal Pressure Differential | > +8 Pa | > -2.5Pa |

FIG. 9A

| Air pressure relative to adjacent areas | Positive |
|---|---|
| Minimum Air exchanges of outside air per hour | 4 |
| Minimum total air exchanges per hour | 20 |
| Air re-circulated by means of room units? | NO |
| Relative Humidity | 20-60 percent |
| Design Temperature | 68-75 Degrees F |

FIG. 9B

ENVIRONMENTAL SENSOR DEVICE WITH ALARMS

BACKGROUND

Air quality may be affected by a wide range of factors including temperature, humidity, air-flow, occupancy, particulate counts, the presence of various chemical and biologic materials, and/or the like. Certain types of locations may need to maintain a standard of air quality. For example, poor air quality in a health care facility such as a hospital may lead to unnecessary infections. Poor air quality in a semiconductor manufacturing facility may lead to unnecessary imperfections in manufactured products. Poor air quality in a housing and/or office environment may lead to long term exposure to harmful elements that may lead to cancer or other disorders. Air quality may be managed using controlling factors such as, for example, air flow, temperature, particulate counts, and humidity.

BRIEF DESCRIPTION OF THE SEVERAL VIEWS OF THE DRAWINGS

Example

Example

Example

Example

Example

Example

Example FIG. 7 is a screen shot of a threshold setup interface as per an aspect of an embodiment of the present invention.

Example FIG. 8A and FIG. 8B are charts showing contamination values for various particle sizes that may be employed in configuring aspects of an embodiment of the present invention.

Example FIG. 9A and FIG. 9B are charts showing example various healthcare facility guidelines that may be employed in configuring aspects of an embodiment of the present invention.

Example

DETAILED DESCRIPTION OF EMBODIMENTS

Some of the various embodiments of the present invention measure and report environmental air quality.

Figure 1:
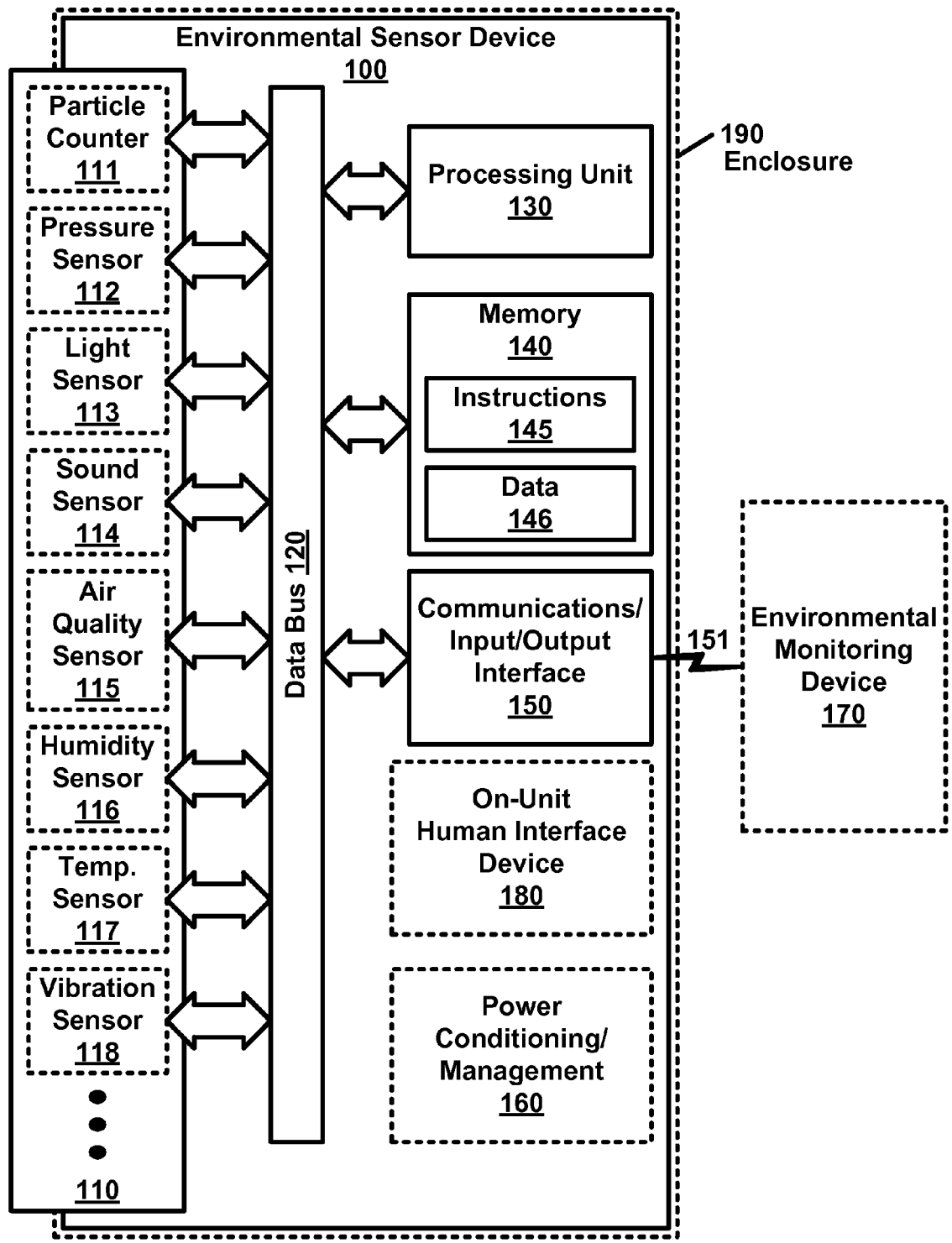
FIG. 1 is a block diagram illustrating an environmental sensor device as per an aspect of an embodiment of the present invention.

Example FIG. 1 is a block diagram illustrating an environmental sensor device 100 as per an aspect of an embodiment of the present invention. Embodiments of the environmental sensor device 100 may comprise a data bus 120, a multitude of sensors 110, at least one processing unit 130, at least one communications interface 150, and memory 140.

A data bus 120 is a communication system that transfers data between components inside or between electronic device(s). According to some of the embodiments, data bus 120 may include various hardware components (wire, optical fiber, etc.) and associated software, including communication protocols. Data buses may include parallel electrical wires with multiple connections. Data bus 120 may include a physical arrangement of electronic components and connections to provide the logical functionality of a parallel electrical bus. Some embodiments of data bus 120 may employ both parallel and bit serial connections and may be wired in either a multi-drop (electrical parallel) or daisy chain topology, or connected by switched hub(s) (e.g. as in the case of Universal Serial Bus (USB)).

The data bus 120 may be an internal or external data bus. Some embodiments of an internal bus may include a memory bus, a system bus, a Front-Side-Bus, a combination thereof, and/or the like. An internal bus may connect internal components of an electronic device such as a processing unit 130, memory 140, communications interface 150, human interface 180, power conditioning/management device 160, and/or the like. Therefore, an internal data bus may also be referred to as a local bus because it may connect to local devices. An external bus (or expansion bus) may include electronic pathways to connect different external devices, such as external sensor(s), external processing device(s), external printer(s), external memory device(s), and/or the like. Examples of external buses may include USB, Ethernet, RS-232, and/or the like.

At least one processing unit 130 may be connected to the data bus. A processing unit 130 may include hardware configured to execute the instructions of a computer program by performing the basic arithmetical, logical, and input/output operations within a system. In some embodiments, a processing unit 130 may comprise a central processing unit (CPU) with associated hardware (e.g. power, input/output, data bus interface, display, etc.). In other embodiments, a processing unit 130 may comprise a microcontroller.

A microcontroller (sometimes abbreviated μC, uC or MCU) is a small computer on a single integrated circuit containing a processor core, memory, and programmable input/output peripherals. Example microcontrollers include, but are not limited to: an Intel 8051 family microcontroller, a Freescale 6811 family microcontroller, an ARM Cortex-M family core processor, an Atmel AVR family microcontroller, an STMicroelectronics STM32 microcontroller, and/or the like.

An input/output/communications interface 150 may be connected to the data bus and configured to communicate with at least one external monitoring device. An input/output/communications interface 150 may be employed to communicate sensor data (raw and/or processed) to at least one external device such as, but not limited to: an external environmental monitoring device 170, another environmental sensor device 100, a server, Software as a Service (SaaS), a smart device, a cell phone interface, a web interface, a combination thereof, and/or the like. An input/output/communications interface 150 may be configured to accept commands from at least one external device such as, but not limited to: an external environmental monitoring device 170, another environmental sensor device 100, a server, an SaaS, a smart device, a cell phone interface, a web interface, a combination thereof, and/or the like.

A communications interface 150 may comprise an electronic circuit configured to a specific communications standard to enable one machine to telecommunicate with another machine. Examples of communications standards include wired or wireless communications interfaces. Examples of wired communications standards include Ethernet, General Purpose Instrument Bus (GPIB), RS-232, RS-422, RS-485, Serial peripheral interface (SPI), an inter-integrated circuit interface (I2C), FireWire™, USB, and/or the like.

Some wired interfaces may provide power. An example of such an interface is a Power over Ethernet (PoE) interface. PoE describes any of several standardized or ad-hoc systems which pass electrical power along with data on Ethernet cabling. This allows a single cable to provide both data connection and electrical power to devices such as wireless access points, sensor devices, or remote processing devices. (The term remote is used here in a relative form to mean remote from a power source). Another example of a wired interface that may deliver power to a device is USB. However, unlike USB devices, PoE may allow for longer cable lengths. Power may be carried on the same conductors as the data, or it may be carried on dedicated conductors in the same cable.

There are several common techniques for transmitting power over Ethernet cabling. Two of them have been standardized by The Institute for Electrical and Electronic Engineers (IEEE) standard IEEE 802.3. Since only two of the four pairs of wires on a 10BASE-T connector may be needed for 10BASE-T or 100BASE-TX, power may be transmitted on the unused conductors of a cable. In the IEEE standards, this is referred to as Alternative B. Power may also be transmitted on the data conductors by applying a common-mode voltage to each pair. Because Ethernet may use differential signaling, this may not interfere with data transmission. A common mode voltage may be extracted using the center tap of the standard Ethernet pulse transformer. This is similar to the phantom power technique commonly used for powering audio microphones. In the IEEE standards, this is referred to as Alternative A.

In addition to standardizing existing practice for spare-pair and common-mode data pair power transmission, the PoE may also provide for signaling between the power source equipment (PSE) and powered device (PD). This signaling may allow the presence of a conformant device to be detected by the power source, and may allow the device and source to negotiate the amount of power required or available.

According to some of the various embodiments, the communications interface 150 comprises a wireless communications interface. Examples of wireless communications interfaces include, but are not limited to: Wi-Fi, Bluetooth™, radio, optical and cellular interfaces. The wireless communications interface may be configured to transfer information between two or more points that are not connected by an electrical conductor. Common wireless technologies use radio. Radio wave distances may be dependent on factors such as transmission signal wavelength, signal strength, encoding technique, environmental attenuation factors, combinations thereof, and/or the like. Other methods of achieving wireless communications may include the use of other electromagnetic wireless technologies, such as light, magnetic, or electric fields or the use of sound.

According to some of the various embodiments, the communications interface 150 comprise input/output configurations. Input/output configurations (often referred to as I/O or IO) include circuitry (sometimes in combination with software and/or firmware) to enable communication between an information processing system and the outside world, possibly a human or another information processing system. Inputs are the signals or data received by the system, and outputs are the signals or data sent from it. I/O devices may employ interface 150 to communicate with various embodiments. For instance, a keyboard or a mouse may be an input device(s) for various embodiments, while monitors and printers may be an output device(s) for various embodiments. Other example devices, such as modems and network cards, may serve for both input and output.

The designation of a device as either input or output depends on the perspective. Mouse and keyboards convert physical human user output movements into signals that various embodiments may understand. The output from these devices may be input for various embodiments. Similarly, printers and monitors take as input signals that various embodiments output. The I/O devices may convert data to representations that human users can see or read. For a human user the process of reading or seeing these representations is receiving input. Additional examples of devices that may be employed through a communications/input/output Interface include, but are not limited to: memory-mapped I/O, device drivers, secondary storage, sensors, and actuators.

Memory 140 may include physical device(s) used to store programs (sequences of instructions 145) or data 146 (e.g. program state information) on a temporary or permanent basis for use by other elements in environmental sensor device 100 such as processing unit 130, communications interface 150, sensors 110, and/or the like. Memory 140 may comprise instruction segment(s) 145 and/or data segment(s) 146. Memory 140 may include primary high speed memory (e.g. Random Access memory (RAM), Read-only Memory (ROM)), and/or secondary memory, which may include physical devices for program and data storage which are slow to access but offer higher memory capacity. The term storage may include devices such as, but not limited to: tape, magnetic disks and optical discs (CD-ROM and DVD-ROM). If needed, primary memory may be stored in secondary memory employing techniques such as "virtual memory."

Primary memory may be an addressable semiconductor memory, i.e. integrated circuits consisting of silicon-based transistors accessible to processing unit 130 via data bus 120. Semiconductor memory may include volatile and/or non-volatile memory. Examples of non-volatile memory are flash memory (sometimes used as secondary computer memory and sometimes used as primary computer memory) and ROM/PROM/EPROM/EEPROM memory (used for firmware such as boot programs). Examples of volatile memory are primary memory (typically dynamic RAM (DRAM), and fast CPU cache memory (typically static RAM (SRAM), which is fast but energy-consuming and offers lower memory capacity per area unit than DRAM).

The instruction segment may include computer readable instructions 145 configured to cause at least one processing unit 130 to, among other tasks: collect sensor data from at least one of the multitude of sensors 110, generate processed sensor data from the sensor data, and generate a report of processed sensor data that exceeds at least one threshold.

The multitude of sensors 110 may be connected to data bus 120. A sensor is a converter device that measures a physical quantity and converts it into a representation that may be read by an observer or by an observer device. For example, a thermocouple may convert temperature to an output voltage which may be converted by an analog to digital converter into a digital representation of the temperature. The digital representation may be read and/or processed by a device such as, for example, processing unit 130. For accuracy, some sensors may be calibrated. A sensor is a device, which responds to an input quantity by generating a functionally related output, for example, in the form of an electrical or optical signal. A sensor's sensitivity may indicate how much the sensor's output changes when the measured quantity changes. Some sensors may have high sensitivities to measure small changes. Other sensors may have lower sensitivities to measure larger changes.

The multitude of sensors 110 may comprise, but are not limited to: particle counter(s) 111, pressure sensor(s) 112, light sensor(s) 113, sound sensor(s) 114, air quality sensor(s) 115, humidity sensor(s) 116, temperature sensor(s) 117, vibration sensor(s) 118, combinations thereof, and/or the like. Pressure sensors(s) 112 may comprise differential pressure sensor(s). Various embodiments may include different combinations of sensors 110. For example, some embodiments may focus on particulate contamination and include a particle counter that may comprise a pressure sensor. Particulate count may be a measure of the cleanliness of an environment. Other embodiments may focus on patient satisfaction and include light sensor(s) 113, sound sensor(s) 114, air quality sensor(s) 115, humidity sensor(s) 116, and temperature sensor(s) 117. More inclusive embodiments may include combinations of sensors found in both particulate contamination and patient satisfaction embodiments. It is envisioned that various combinations of sensors may be configured in various embodiments to serve the various and additional needs of a specific location.

As noted earlier, some embodiments may monitor factors related to patient satisfaction. Such embodiments may be configured to, for example, monitor and baseline sound levels, light levels, air quality, humidity, combinations thereof, and/or the like.

The multitude of sensors 110 may comprise additional sensors. By way of example and not limitation, additional sensors may include: particle reflection sensor(s), albido sensor(s), particle spectroscopy sensor(s), particle imagery sensor(s), laser induced fluoroscopy sensors, combinations thereof, and/or the like. Laser induced fluoroscopy sensors and/or similar sensors may be employed to identify organic particles. Sensors may be internal or external to environmental sensor and/or monitor device(s). Sensors that are located external to an environmental sensor and/or monitor device(s), may be connected via a wired (e.g. cable) or wireless (e.g. Wi-Fi) connection. Sensors may have remote components that are external to a main component. Remote in this sense means physically separate from the main component. The remote component may be connected via a wired (e.g. cable) or wireless (e.g. Wi-Fi) connection.

According to some of the various embodiments, particle counter(s) 111 may comprise multiple channels for counting particles of different sizes. The multiple channels may include one or more of, but not limited to: a channel for particles that are approximately 10 um and less, a channel for particles that are approximately 5 um and less, a channel for particles that are approximately 1 um and less, a channel for particles that are approximately 0.5 um and less, and a channel for particles that are less than 0.5 um. Some of the channels may be optional channels. Some of the various embodiments may include a particle counter(s) 111 that may comprise channels configured to measure particles in different sizes and/or different ranges.

Some of the various particle counter(s) 111 may count particles as particles per unit volume. Some of the various particle counter(s) 111 may report counts in a cumulative counting mode. A cumulative counting mode may be configured to accumulated particle data in multiple (all or selected) particle size channels. Some of the various particle counter(s) 111 may report counts in a differential counting mode. Differential counting may report particle data as the number of particles in a specific particle size channel. Similarly, some of the various particle counter(s) 111 may report counts in an ISO class mode. ISO class counting may report particle counts according to defined ISO classes. ISO codes may provide a mechanism to quantify particulate matter by size. ISO codes are established by the International Organization for Standardization, an international standards organization based in Geneva, Switzerland. Under ISO code system(s), code numbers are set up, each representing a given range of particles per unit volume. Smaller code numbers correlate to smaller numbers of particles. ISO class counting may require assigning bin sizes to one or more ISO class numbers. ISO class counting may report particle counts by ISO code numbers in either cumulative and/or differential counting modes.

Some of the various particle counter(s) 111 may have at least one channel. Each of the channel(s) may be configured to: have a channel size; and count particles that are equal or greater than the channel size. Particle counts may be converted into processed sensor data. Processed sensor data may ignore sensor data from the particle counter(s) 111 for specific sized particles. The processed sensor data may also perform one or more statistics on raw particle counts. A statistic is a process by which more than one particle count may be combined into a resultant value. A statistic may include mathematical analysis, linear algebra, stochastic analysis, differential equations, measure-theoretic probability theory, and/or the like.

Some of the various embodiments may employ a pressure sensor(s) 112 configured to measure the pressure of gases (e.g. air) in one or more location(s). Pressure is an expression of the force required to stop a fluid from expanding and is usually stated in terms of force per unit area. Pressure sensor(s) may act as a transducer to generate a signal as a function of the pressure imposed. Such a signal may be electrical, digital, optical, and/or the like. Some of the various pressure sensors 112 may be configured to measure pressure in a dynamic mode for capturing changes in pressure.

Pressure sensor(s) 112 may comprise differential pressure sensor(s). A differential pressure sensor may include a pressure measuring device that is configured to measure and report the relative difference in pressure in two separate areas. So, for example, the differential pressure sensor may be configured to measure the differential pressure between a remote area and a local area. A differential pressure sensor may measure the difference between two pressures, one connected to each side of the sensor. Differential pressure sensors may be used to measure many properties, such as pressure drops across air filters and/or flow rates between physical areas (by measuring the change in pressure across a restriction such as a wall).

According to some of the various embodiments, pressure sensor(s) 112 may comprise and/or be configured as differential pressure sensor(s). A multitude of pressure sensor(s) 112 may be configured as a differential pressure sensor. For example, a differential pressure sensor may be configured employing at least two static pressure sensors.

According to some of the various embodiments, a differential pressure sensor may be configured to measure a remote pressure via tube. According to other embodiments, a differential pressure sensor may be configured to measure a remote pressure via static sensor pressure tip. According to yet other embodiments, a differential pressure sensor may be configured to measure a remote pressure via a signal communicated from a remote static pressure sensor. Some of the various differential pressure sensor(s) may be configured to measure a local pressure via a local port.

Facilities such as healthcare institutions may place pressure sensors in key rooms that may or may not be networked. Some pressure sensors may be as simple as a ball in a tube.

Some facilities such as healthcare institutions may also employ a handheld particle counter in key rooms to "baseline" particle counts. However, it may be useful to network the pressure sensor to track room pressure 24/7, baseline the room pressure, and observe events when no one is available to monitor the pressure sensor. It may be useful to network the particle counter to track room particle counts 24/7, baseline the room particle counts, and observe events when no one is available to monitor the particle counter. When a particle counter is only read periodically (e.g. once a day, week, month or quarter), it may provide little information regarding what happened in between sampling times.

From an infection control standpoint, it may be useful to know two things about key rooms (e.g. operating rooms, immune compromised patient rooms, airborne isolation rooms), namely that pressure is maintained and that the facility air filtering system is properly removing particulates. Some of the various embodiments, by combining these two functions, particularly in a networked manner with the ability to post-process monitored data, provides an improved level of maintaining facility air quality.

Light sensor(s) 113 may be employed in some embodiments to measure ambient light in a location. The light may be measured in a unit such as, but not limited to Lux. The light sensor(s) 113 may be referred to as photo sensors or photo detectors and may be configured to sense and/or measure light and/or other electromagnetic energy. Examples of light sensors include, but are not limited to: active-pixel sensors (APSs); charge-coupled devices (CCD), reverse-biased LEDs, photoresistors, light dependent resistors (LDR), photovoltaic cells, solar cells, photodiodes, photomultiplier tubes, phototubes, phototransistors, quantum dot photoconductors, and/or the like.

Sound sensor(s) 114 may be employed in some embodiments to measure ambient sound in a location. Sound Sensor(s) 114 may comprise an acoustic-to-electric transducer or sensor that converts sound in air into an electrical signal. Sound sensors 114 may include various types of acoustic, sound and/or vibration sensor 118, such as, but not limited to a device employing: electromagnetic induction (dynamic microphones), capacitance change (condenser microphones), piezoelectricity (piezoelectric microphones) to produce an electrical signal from air pressure variations, a combination thereof, and/or the like. Sound sensors 114 employed by various embodiments may comprise a condenser microphone, an electret condenser microphone, a dynamic microphone, a ribbon microphone, a carbon microphone, a piezoelectric microphone, a fiber optic microphone, a laser microphone, a liquid microphone, a MEMS microphone, and/or the like. Sound sensor(s) 114 may be connected to a circuit such as a preamplifier circuit, an amplifier circuit, signal processing circuit, and/or the like. The circuit may include at least one wide dynamic range logarithmic amplifier, at least one A-weighted audio filter, a combination thereof, and/or the like.

The machine readable instructions 145 may include machine readable instructions configured to cause the at least one processing unit 130 to integrate or otherwise process sound sensor data. The processing may include integrating the sound sensor data with a sliding peak-hold function.

Some of the various embodiments may employ at least one humidity sensor(s) 116. A humidity sensor 116 may be configured to detect and measure atmospheric humidity. Some of the various humidity sensors 116 may comprise a resistance or capacitance element that varies with the surrounding humidity that may be configured to generate an analog (e.g. current or voltage) and/or digital value corresponding to fluctuations in humidity. Some of the various humidity sensors 116 may sense relative humidity. This means that the humidity sensor 116 measures both air temperature and moisture. Relative humidity may be, according to some embodiments, expressed as a ratio of actual moisture in the air to the highest amount of moisture air at that temperature can hold. The warmer the air is, the more moisture it can hold, so relative humidity changes with fluctuations in temperature. A common type of humidity sensor uses a "capacitive measurement." This system may rely on electrical capacitance, or the ability of two nearby electrical conductors to create an electrical field between them. The sensor itself may be configured using two metal plates with a non-conductive polymer film between them. The film may collect moisture from the air causing changes in the voltage between the two plates. The changes in voltage may be converted into digital readings showing the amount of moisture in the air.

Some of the various embodiments may employ at least one temperature sensor 117. A temperature sensor 117 may comprise a device that measures temperature or a temperature gradient using a variety of different principles. A temperature sensor 117 may comprise a device in which a physical change occurs with temperature, plus a device for converting the physical change into a measurable value. Examples of devices in which a physical change occurs with temperature include, but are not limited to: bi-metallic stemmed thermometers, thermocouples, infrared thermometers, and thermistors.

Some of the various embodiments may employ at least one air quality sensor 115. Some of the various air quality sensors may comprise at least one CO2 sensor. A CO2 sensor may measure CO2 as parts per million and/or other suitable quantity. Alternative embodiments may comprise at least one hazardous gas sensor. A hazardous gas sensor may measure the presence of gases such as hydrogen peroxide, chlorine, and/or the like. A hazardous gas sensor may employ sensors such as, but not limited to: infrared (IR) point sensor(s), infrared imaging sensor(s), ultrasonic sensor(s), electrochemical gas sensor(s), holographic gas sensor(s), and semiconductor sensor(s).

An electrochemical gas sensor may be configured to allow gases to diffuse through a porous membrane to an electrode where the gas may be either oxidized or reduced. A variable amount of current may be produced determined by how much of the gas is oxidized at the electrode. The sensor may be able to determine the concentration of the gas. Electrochemical gas sensors may be customized by changing the porous barrier to allow for the detection of a certain gas concentration range.

An IR point sensor may employ radiation passing through a volume of measured gas to detect the presence of specific gasses. Energy from the radiation may be absorbed as the measured gas passes through the gas at certain wavelengths. The range of wavelengths that is absorbed depends on the properties of the specific gas. Carbon monoxide absorbs wavelengths of about 4.2-4.5 μm, for example. This is approximately a factor of 10 larger than the wavelength of visible light, which ranges from 0.39 μm to 0.75 μm for most people. The energy in this wavelength may be compared to a wavelength outside of the absorption range. The difference in energy between the two wavelengths may be proportional to the concentration of specific gas present.

An infrared imaging sensor may be configured to scan a laser across the field of view of a scene and look for backscattered light at the absorption line wavelength of a specific target gas. Passive IR imaging sensors, on the other hand, may be configured to measure spectral changes at each pixel in an image and look for specific spectral signatures which indicate the presence of target gases.

Semiconductor sensors may be configured to detect gases by a chemical reaction that takes place when a gas comes in contact with the sensor. Tin dioxide is one of the various materials that may be employed in semiconductor sensors. The electrical resistance in the sensor may decrease when it comes in contact with the monitored gas. The resistance of tin dioxide may be around 50 kΩ in air but can drop to around 3.5 kΩ in the presence of 1% methane. This change in resistance may be employed to calculate a gas concentration. Semiconductor sensors may be employed to detect, for example, hydrogen, oxygen, alcohol, and harmful gases such as carbon monoxide.

Ultrasonic gas detectors may be configured to employ acoustic sensors to detect changes in the background noise of an environment in order to detect a probability that gas may be leaking into an environment that has a pressurized gas line, such as for example, an operating room, a patient room, and/or the like. Since some gas leaks occur in the ultrasonic range of 25 kHz to 10 MHz, the sensors may be able to easily distinguish these frequencies from background noise which occurs in the audible range of 20 Hz to 20 kHz. Ultrasonic gas leak sensors may produce an alarm when there is an ultrasonic deviation from the normal condition of background noise. Despite the fact that ultrasonic gas leak sensors may not measure gas concentration directly, the device may still be able to determine the leak rate of an escaping gas. By measuring its ultrasonic sound level, the detector may be able to determine the leak rate, which may depend on the gas pressure and size of the leak. The bigger the leak, the larger its ultrasonic sound level may be.

Holographic gas sensors may be configured to employ light reflection to detect changes in a polymer film matrix containing a hologram. Since holograms reflect light at certain wavelengths, a change in their composition may generate a colorful reflection indicative of the presence of gas molecule(s). A holographic sensor may be configured with illumination source(s) such as white light or lasers, and a detector such as a CCD detector or the like.

Some of the various embodiments may comprise an on-unit human interface device 180. A human interface device 180 is a type of electronic device that interacts directly with, and most often takes input from, humans and may deliver output to humans. A human interface device may connect to an electronic device that is integrated with the environmental sensor device 100. Examples of electronic devices that interact directly with a human include, but are not limited to: mice, keyboards, joysticks, displays, switches, speakers, sound (and voice) synthesizers, smart devices, color LED(s), LCD display(s), touchpad(s), touchscreen(s), audio alarms, alerts, combinations thereof, and/or the like. On-unit human interface device 180 may comprise such electronic devices discretely or in combination. Some of the on-unit human interface device 180 components may be embedded in the body of one or more of the multitude of sensors 110, an environmental sensor device 100, an environmental monitoring device 170, an enclosure 190, combinations thereof, and/or the like.

Some of the various embodiments may comprise power conditioning and/or management devices 160. A power conditioning device (also known as a line conditioner or power line conditioner) is a device configured to improve the quality of power delivered to an environmental sensor device 100. A power conditioning device may employ one or more mechanisms to deliver a voltage of levels and characteristics that enable other components (e.g. processing unit 130, memory 140, interface 150, data bus 120, and/or the like) to function properly. In some embodiments, a power conditioner may comprise a voltage regulator with at least one other function to improve power quality (e.g. power factor correction, noise suppression, transient impulse protection, etc.). According to some of the embodiments, a power conditioner may be configured to smooth an incoming sinusoidal alternating current (AC) wave form and maintain a constant voltage over varying loads.

Some of the various embodiments of power conditioning and/or management devices 160 may manage power for all or part of the environmental sensor device 100. According to some embodiments, the power management may comprise changing a power state for all or part of the components in the environmental sensor device 100. Some power states may include, but are not limited to: on, off, inactive, low-power, medium power, high power, and/or the like. Power management may comprise monitoring the power state for: one or more power sources (e.g. AC power, batteries, and/or the like), all or part of the components in the environmental sensor device 100, and/or the like. Power management may manage the charging of batteries and/or the switching between power sources.

Environmental sensor device(s) 100 may communicate to environmental monitoring device(s) 170 via a communications link 151. The communications link 151 may communicate over a data network.

According to some of the various embodiments, all or part of environmental sensor device 100 may be disposed in an environmental enclosure 190. Enclosure 190 may be a sealed enclosure to protect environmental sensor device 100, at least some of the sensors 110, and/or the like in environments such as a lab, a pharmacy, areas subject to wash-down, combinations thereof, and/or the like. The enclosure 190 may be configured to a National Electrical Manufacturers Association (NEMA) standard (e.g. NEMA 4). NEMA defines standards for various grades of electrical enclosures typically used in industrial applications. Each grade is rated to protect against designated environmental conditions. A typical NEMA enclosure might be rated to provide protection against environmental hazards such as water, dust, oil or coolant or atmospheres containing corrosive agents such as acetylene or gasoline. For example, a NEMA 4 enclosure is defined as a watertight (weatherproof) container configured to exclude at least 65 gallons per minute (GPM) of water from a 1-in. nozzle delivered from a distance not less than 10 ft. for 5 min. A NEMA 4× enclosure generally has corrosion resistance.

Enclosure 190 may include caps or covers for air inlet(s). The walls of enclosure 190 may retain a fire and smoke barrier rating. Enclosure 190 may be configured for various mounting positions such as, but not limited to: a ceiling mounted position, a plenum, a tube, a wall, combinations thereof, and/or the like. According to some of the various embodiments, enclosure 190 may be configured to maintain a fire and smoke barrier rating of location (e.g. ceiling) in which the enclosure 190 is mounted. Enclosure 190 may also be configured to enable placement of sensor(s) in out-of-the-way locations, including, for example, facilitating tubing to adjacent locations.

Figure 2:
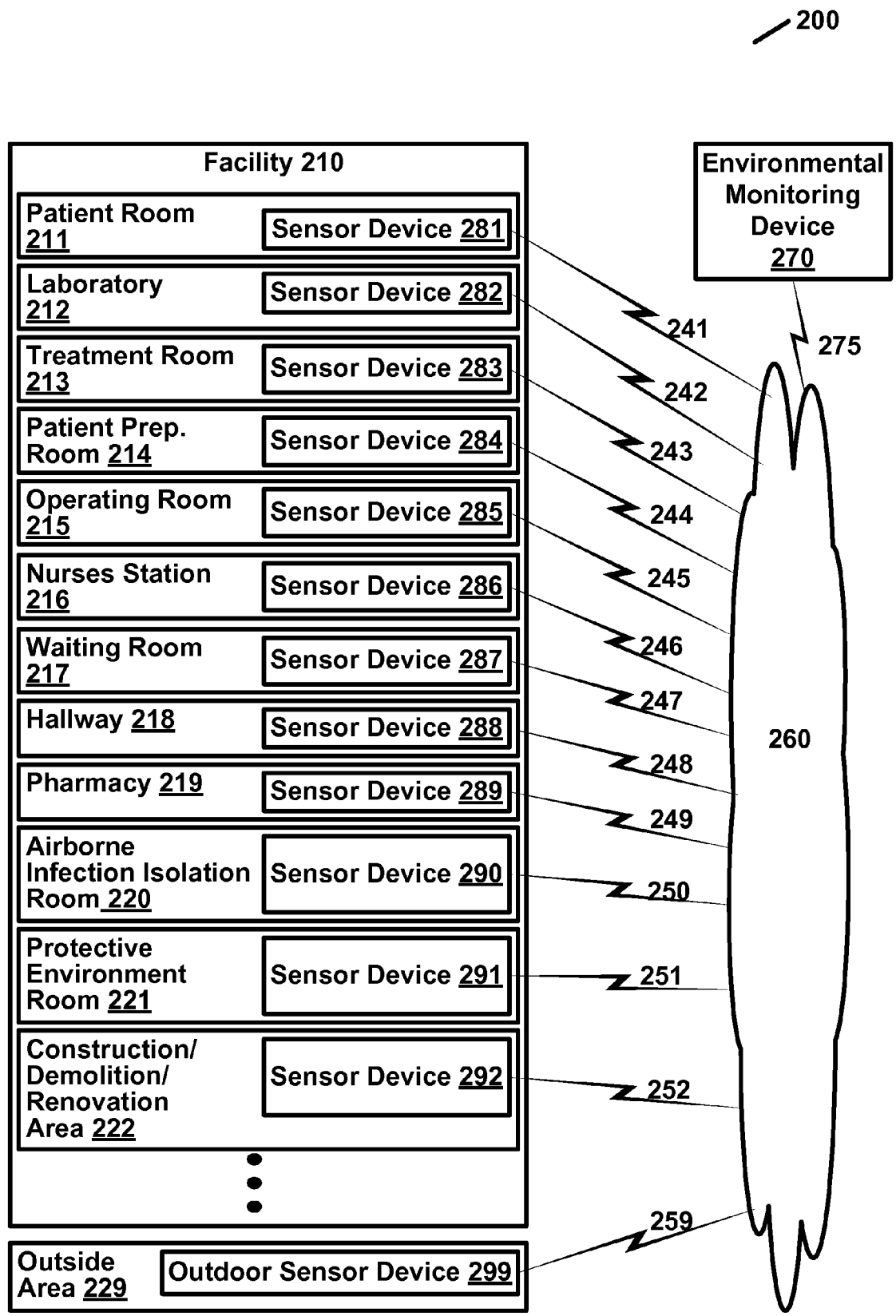
FIG. 2 is a block diagram illustrating environmental sensing system in a facility as per an aspect of an embodiment of the present invention.

FIG. 2 illustrates an example configuration 200 of multiple environmental sensor devices (e.g. 281, 282, 283, 284, 285, 286, 287, 288, 289, 290, 291, 292, and 299) located in various locations (e.g. 211, 212, 213, 214, 215, 216, 217, 218, 219, 220, 221, 222 and 229) throughout a facility 210 communicating with an environmental monitoring device 270 over communication channels (e.g. 241, 242, 243, 244, 245, 246, 247, 248, 249, 250, 251, 252, 259 and 275) via network 260.

This configuration is presented for example purposes only. It is expected that the use of environmental sensor device(s) 100 may be configured various topologies. As illustrated in this example, a facility 210 (e.g. a health care facility) may have various locations dedicated for differing purposes. Example locations for which there may be a desire to monitor environmental quality include, but are not limited to: patient rooms) 211, laborator(ies) 212, treatment room(s) 213, patient preparation room(s) 214, operating room(s) 215, nurses station(s) 216, waiting room(s) 217, hallway(s) 218, pharmac(ies) 219, airborne infection isolation room(s) 220, protective environment room(s) 221, construction/demolition/renovation area(s) 222 and outside area(s) 229.

Each of these various locations may have different environmental quality requirements. For example, the environmental quality in a waiting room 217 and hallway 218 may not need to be as stringent as the environmental quality in an operating room 215. In addition to air quality, noise and light levels may be more important to manage in a patient room 211 than, for example, in a waiting room 217. It may also be desired to independently monitor each of the independent locations. As illustrated: patient room 211 may be configured to be monitored by environmental sensor device 281, laboratory 212 may be configured to be monitored by environmental sensor device 282, treatment room 213 may be configured to be monitored by environmental sensor device 283, patient preparation room 214 may be configured to be monitored by environmental sensor device 284, operating room 215 may be configured to be monitored by environmental sensor device 285, nurses station 216 may be configured to be monitored by environmental sensor device 286, waiting room 217 may be configured to be monitored by environmental sensor device 287, hallway 218 may be configured to be monitored by environmental sensor device 288, and a location outside the facility 210 may be configured to be monitored by an outdoor environmental sensor device 299. Each of the environmental sensor devices (e.g. 281, 282, 283, 284, 285, 286, 287, 288, 289, 290, 291, 292, and 299) may then independently report air quality values to one or more environmental monitoring device(s) 270 via a network 260.

Figure 3:
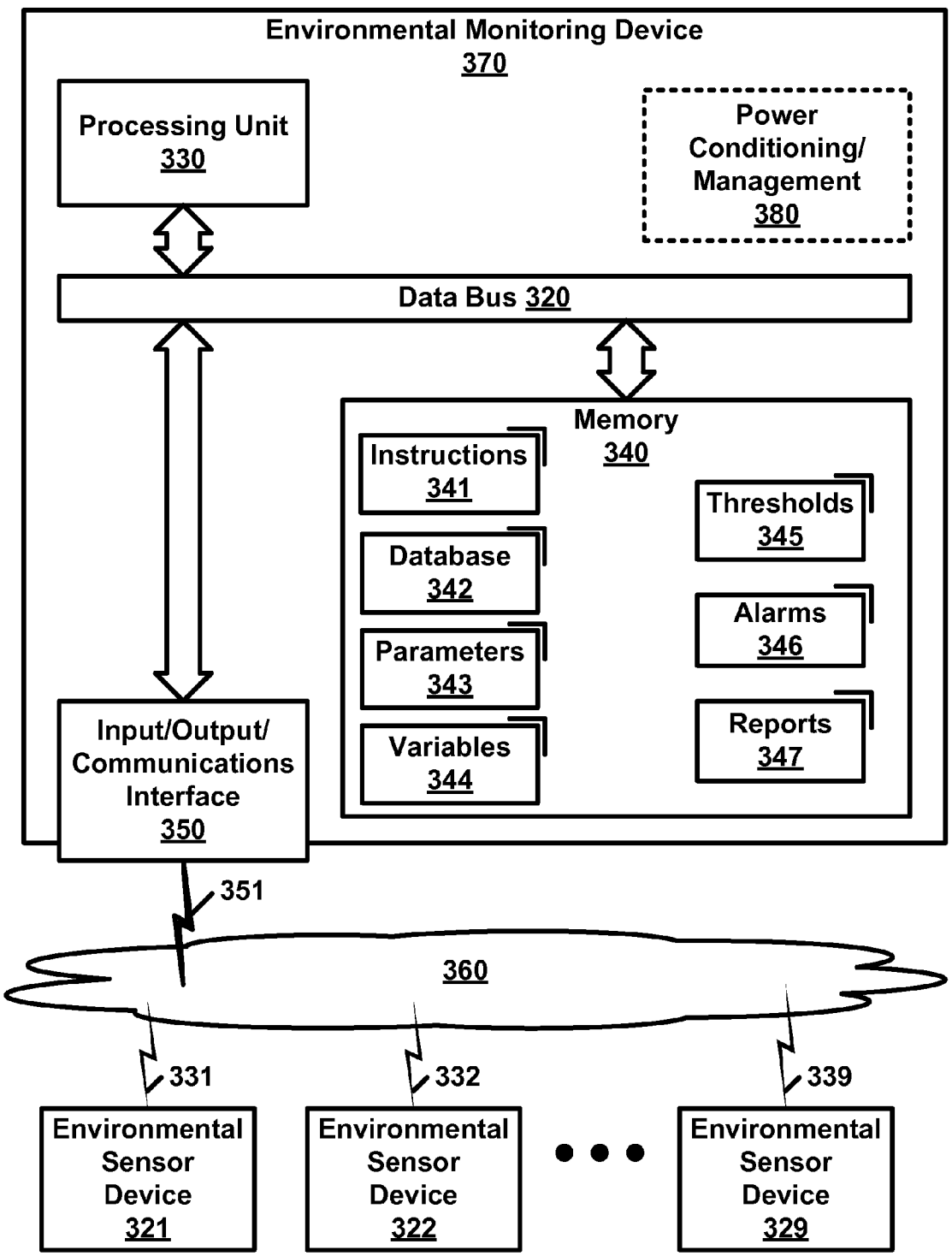
FIG. 3 is a block diagram illustrating an external environmental monitoring device as per an aspect of an embodiment of the present invention.

According to some of the various embodiments, an external monitoring device 170 may be employed to monitor environmental sensor device(s) 100. FIG. 3 illustrates an example environmental monitoring device 370 as per an aspect of environmental monitoring device 170. The example environmental monitoring device 370 may comprise a data bus(es) 320, processing unit(s) 330 connected to the data bus(es) 320, input/output/communications interface(s) 350, and memory 340. As shown in this illustration, example environmental monitoring device 370 may also comprise power conditioning/management module 380. The data bus(es) 320, processing unit(s) 330, input/output/communications interface(s) 350, memory 340, and power conditioning/management module 380 components are similar to the previously disclosed elements in environmental sensor device 100. So for example, data bus(es) 320 may be similar to data bus(es) 120, processing unit(s) 330 may be similar to processing unit(s) 130, input/output/communications interface(s) 350 may be similar to input/output/communications interface(s) 150, memory 340 may be similar to memory 140, and power conditioning/management module 380 may be similar to power conditioning/management module 160. The phrase "may be similar to" means that the hardware, software in combination with hardware, functionality, and/or the like may be, according to some embodiments, compatible and/or the same. According to some of the various embodiments, components and combinations of components from the example environmental sensor device 100 and example environmental monitoring device 370 may be employed in other embodiments of example environmental sensor device(s) and example environmental monitoring device(s).

As illustrated in this example embodiment, the input/output/communications interface 350 may be configured to communicate with at least one environmental sensor device (321, 322 . . . 329) over communications links (351, 331, 332 . . . 339) via network 360. The communications may comprise sensor data from at least one environmental sensor device (321, 322 . . . 329). Additionally, the communications may comprise other types of information including commands, analysis, status, and/or the like.

Network 360 may comprise a telecommunications network configured to allow electronic devices to exchange data. In such a network, electronic devices such as environmental monitoring device 370 and environmental sensor devices (321, 322 . . . 329) may pass data to each other along data connections (e.g. 351, 331, 332 . . . 339). The connections (network links) between nodes may be established using either cable media or wireless media. The network 360 may comprise multiple interconnected networks. Examples of networks include the Internet, Wide Area Networks (WANs), Local Area Networks (LANs) and intranet(s). Some of the various networks may be internal to a facility and some of the various networks may be external to a facility. Nodes may comprise electronic devices that originate, route and terminate data. Nodes may include hosts such as environmental monitoring device 370, environmental sensor devices (100, 321, 322 . . . 329), personal computers, phones, servers as well as networking hardware. Two such devices are said to be networked together when one device is able to exchange information with the other device, whether or not they have a direct connection to each other. Network 360 may be configured to support applications such as access to the World Wide Web, shared use of application and storage servers, printers, and fax machines, and use of email and instant messaging applications. Parts of network 360 may differ in the physical media used to transmit data signals, the communications protocols to organize network traffic, the network's size, topology and organizational intent.

Figure 4:
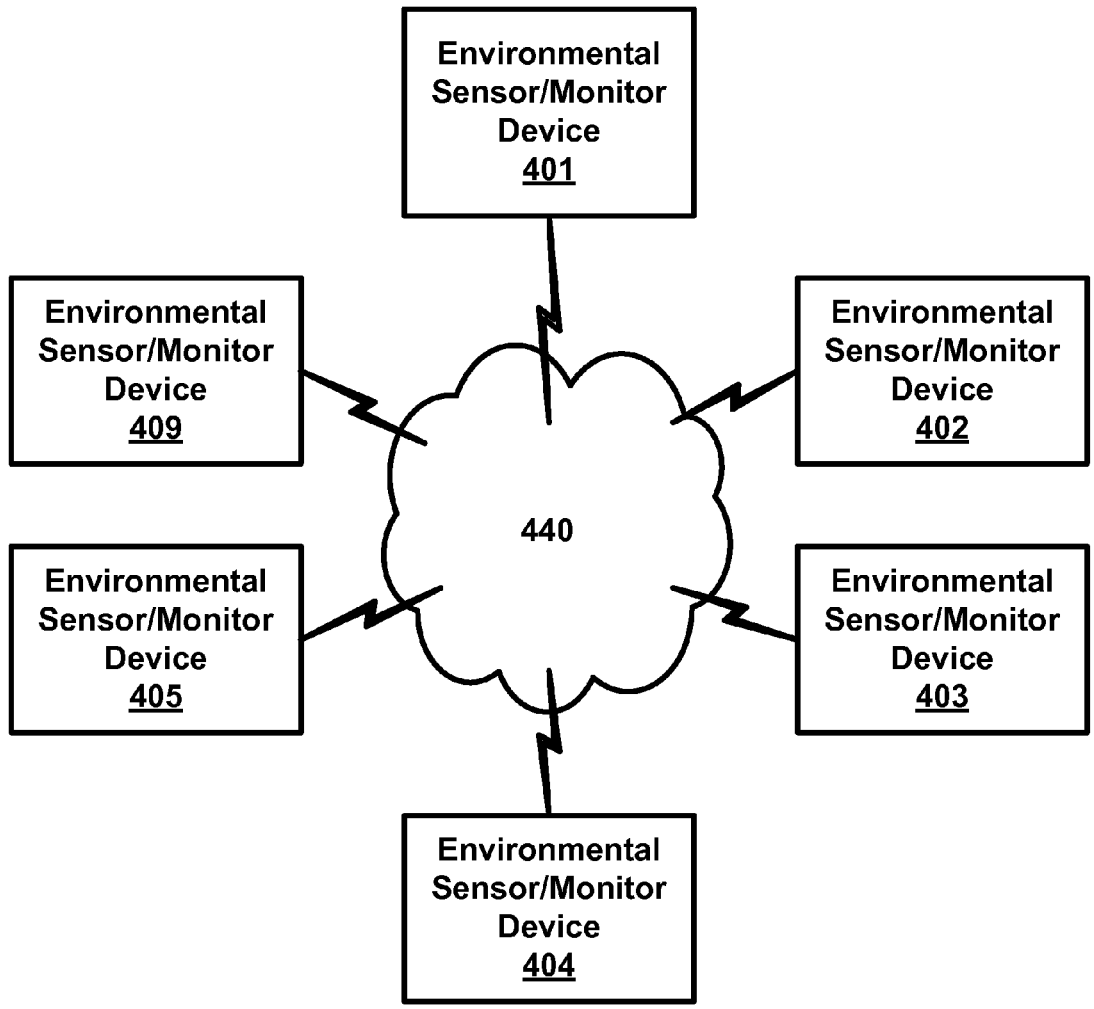
FIG. 4 is a block diagram illustrating a multitude of environmental sensor/monitor device(s) interconnected as a system via network(s) as per an aspect of an embodiment of the present invention.

Example FIG. 4 is a block diagram illustrating a multitude of environmental sensor/monitor device(s) (401, 402, 403, 404, 405 . . . 409) interconnected as a system via network(s) 440. According to some of the various embodiments, some environmental sensor device(s) may also act as an environmental monitoring device. Similarly, according to some of the various embodiments, some environmental monitoring device(s) may also act as an environmental sensor device. In such a configuration, some (or all) of the environmental sensor/monitor device(s) (401, 402, 403, 404, 405 . . . 409) may be configured to communicate data to other environmental sensor/monitor device(s) (401, 402, 403, 404, 405 . . . 409). According to some of the various embodiments, the network may be an organized network, either pre-planned or laid-out according to an organizational scheme. An organizational scheme may include some of the environmental sensor/monitor device(s) (401, 402, 403, 404, 405 . . . 409) in certain locations reporting to other environmental sensor/monitor device(s) (401, 402, 403, 404, 405 . . . 409) in other locations. For example, environmental sensor/monitor device(s) in patient rooms may be configured to report to environmental sensor/monitor device(s) in locations containing facility or healthcare workers.

In yet other embodiments, some (or all) of the environmental sensor/monitor device(s) (401, 402, 403, 404, 405 . . . 409) may connect themselves into an ad hoc network. In such an embodiment, one or more of the some (or all) of the environmental sensor/monitor device(s) (401, 402, 403, 404, 405 . . . 409) may determine some other (or all) of the environmental sensor/monitor device(s) (401, 402, 403, 404, 405 . . . 409) operating within the network and connect to one or more of the other devices forming the ad hoc network configuration. In some embodiments, one or more of the some (or all) of the environmental sensor/monitor device(s) (401, 402, 403, 404, 405 . . . 409) may become master units directing the connections. In yet other embodiments, some (or all) of the environmental sensor/monitor device(s) (401, 402, 403, 404, 405 . . . 409) may each make their own decisions as to which other some (or all) of the environmental sensor/monitor device(s) (401, 402, 403, 404, 405 . . . 409) to attempt to connect. The connections may be made using a protocol. An example protocol may comprise one of the environmental sensor/monitor device(s) (401, 402, 403, 404, 405 . . . 409) sending a request to link to one or more of the other environmental sensor/monitor device(s) (401, 402, 403, 404, 405 . . . 409) and that some (or all) of the environmental sensor/monitor device(s) (401, 402, 403, 404, 405 . . . 409) sending back an affirmative and/or negative reply, leading to a possible data connection.

An environmental monitor device 370 may be a device that is configured to specifically monitor environmental sensor devices. The environmental monitor may be a SaaS program running on a server and accessible on a network. The network may be a local network or public network (e.g. Internet). The Software as a Service may comprise one or more programs configured to receive sensor data, process the sensor data, analyze the sensor data, and/or take actions based upon the sensor data. The programs may be configured to feed results between each other. For example, one SaaS may be configured to receive and filter sensor data. The output of that SaaS may be fed to another SaaS that is configured to run a statistical analysis on filtered sensor data. The output of that SaaS may be communicated to an alarm SaaS that is configured to set various alarms based on the statistical analysis.

According to some of the various embodiments, external monitoring device(s) 370 may comprise at least one environmental monitoring program. Such an embodiment may comprise a particular monitoring program that performs all of the monitoring functions on one machine. However, it is envisioned that such a program may also be configured as a series of programs configured to interact. Some of the programs may run on connected devices. Some of the programs may be environmental sensing programs configured to read sensors. Some of the sensors may be networked sensors.

According to some of the various embodiments, external monitoring device(s) may employ a network based server. The network based server may be accessible via a cloud based network (e.g. Internet). The network based server may host various elements of a monitoring system, such as, but not limited to: databases, SaaS, software monitoring programs and/or hardware, supervisory data acquisition and/or control (SCADA) hardware and/or software, interface drivers, and/or the like.

Memory 340 may include segments to hold different types of electronic data such as, but not limited to: instructions 341, database 342, parameters 343, variables 344, thresholds 345, alarms 346, and reports 347. The instructions 341 may be configured to cause processing unit 330 to perform various actions related to various embodiments.

Instructions 341 may be configured to cause one or more processors to perform actions in support of environmental sensing, environmental monitoring, and/or the like. The actions may be configured to interact with environmental sensor devices, other distributed processing hardware, reporting systems, alarm systems, air handling equipment, gas suppression equipment, and/or the like. The instructions may be in the form of at least one of the following: object code, assembly code, interpretive code, compiled code, linked code, library modules, and/or the like.

According to some of the various embodiments, external monitoring device(s) may employ database(s) 342. A database is an organized collection of data. The database may be configured to store data, for example, for various sensors by location and time. The data may be organized to model aspects of reality in a way that supports processes requiring this information. For example, according to some of the various embodiments, the database may model the environmental characteristics of one or more facilities. For example, some entries for a database may represent characteristics such as particle count in adjacent locations in the facility. The database may also include pressure information for each of these adjacent locations. Using the database 342 as a model, it may be possible to predict the movement of particle from high pressure locations to lower pressure adjacent locations.

Database(s) 342 may be accompanied with database management system(s) (DBMSs) specially designed software application(s) that interact with the user, other application(s), and the database itself to capture and analyze data. A general-purpose DBMS is a software system designed to allow the definition, creation, querying, update, and administration of databases. Well-known DBMSs include MySQL, MariaDB, PostgreSQL, SQLite, Microsoft SQL Server, Oracle, SAP HANA, dBASE, FoxPro, IBM DB2, LibreOffice Base, FileMaker Pro, Microsoft Access and InterSystems Cache. Some of the databases may be of various types such as, but not limited to: operational databases, specific databases, external databases, hypermedia databases, and/or the like. The database 342 may be sized to the number of apparatuses reporting to the at least one external monitoring device 370.

Database(s) 342 may employ at least one database interface. At least one database interface may be configured to display and/or present processed sensor data from the database in, for example, a tabular format, a graphical format, a text format, a query/answer format, and/or the like. A database interface (DBI) may separate the connectivity of a DBMS into a "front-end" and a "back-end." Applications may employ an exposed "front-end" application programming interface (API). An unexposed back-end may convert communicate data and/or instructions between the API and a database and/or related components. These facilities may communicate with specific DBMS (Oracle, PostgreSQL, etc.) via "device drivers." The API may specify how some software components (e.g. database components) interact with each other. In addition to accessing databases, an API may be employed to ease the work of programming graphical user interface components. According to some embodiments, the API may employ a library that includes specifications for routines, data structures, object classes, and variables. In other embodiments, the API may employ remote calls exposed to API consumers.

A device driver (commonly referred to as simply a driver) may comprise a computer program that operates or controls a particular type of device that is attached to a system. The driver may provide a software interface to hardware devices, enabling a database, database interface, operating systems and/or other computer program to access hardware functions without needing to know precise details of the hardware being used. A driver typically communicates with the device through the computer bus or communications subsystem to which the hardware connects (e.g. displays, sensors, memory devices, communication interfaces, and/or the like). When a calling program invokes a routine in the driver, the driver may issue commands to the device. Once the device sends data back to the driver, the driver may invoke routines in the original calling program. Drivers may be hardware-dependent and operating-system-specific. Device drivers may provide the interrupt handling required for any necessary asynchronous time-dependent hardware interface.

Memory may comprise a data segment. The data segment may provide data storage for a database and/or independent storage. The data segment may comprise data storage for sensor data. The sensor data may be raw and/or processed.

Raw data (sometimes referred to as primary data) may comprise data collected from a source such as a sensor. Raw data, generally, has not been subjected to any significant processing or other manipulation. Raw data may, among other possibilities: contain errors; be unvalidated; be in different formats; and uncoded or unformatted. For example, a data input from a pressure sensor may comprise a raw value that represents a pressure measured from the sensor.

Once captured, raw data may be processed into processed sensor data. Processing of the data may involve converting the raw value to a normalized and/or calibrated value. For example, it may be known that a raw value of zero for a particular linear pressure sensor represents 10 pounds per square inch (PSI) and that raw value of 256 represents a 90 PSI. Processing may use this information to convert the raw data value to processed data value that accounts for this conversion. Processed data may also represent the raw data in a format that is compatible with computers and humans to interpret during later processing.

Processed sensor data may comprise variations of data including, but not limited to: real-time sensor data, time-weighted average (TWA) sensor data, short term exposure limit (STEL) sensor data, sensor data collected in a temporal window, combinations thereof, and/or the like. Real-time sensor data denotes sensor data that is fresh (e.g. recently collected and timely). TWA may comprise the average concentration of contaminants over a specified time period (e.g. 3 hours). Mathematically, TWA may represent the integrated area under the concentration curve over time divided by time period. STEL may comprise a TWA exposure over a second period of time (e.g. 15 minutes) which should not be exceeded at any time, even if a longer TWA is within limits. Sensor data collected in a temporal window may represent data measurement collected during a window of time. For example, a temporal window may be defined that collects data for the previous 15 minutes. With such a window, any collected data that is older than 15 minutes may be discarded. According to some embodiments, some processed sensor data may ignore specific sensor data. For example, processed data may ignore outlier data, data during certain temporal windows, data collected while a sensor stabilizes, and/or the like.

According to some of the various embodiments, memory may comprise data storage for threshold data 345. Threshold(s) represent a magnitude or intensity that must be exceeded for a certain reaction, result, or condition to occur. Examples of thresholds include, but are not limited to: a maximum safe pressure level, a period of time where a differential pressure may exceed a specific value, specific sensor data, and/or the like. Thresholds 345 may comprise multiple and distinct thresholds. One or more of the thresholds may exhibit common characteristics. One or more of the thresholds may exhibit uncommon characteristics. At least one threshold comprises a predetermined threshold. A predetermined threshold is a threshold that has been established or decided in advance. Predetermined thresholds may be determined in many ways. For example, at least one of the predetermined thresholds may be determined based upon a standard such as, for example, the U.S. Federal Standard 209E, the international IEST ISO 14644-1 standard, and/or the like. ISO 14644-1 standard for cleanroom is divided into a series of classes referred to as ISO 1, ISO 2 . . . ISO 9. According to some of the various embodiments, at least one predetermined threshold may comprise a reference threshold. The reference threshold may be based at least in part on, for example, ISO 9. According to some of the various embodiments, at least one of the predetermined thresholds may be determined at least in part on a combination of at least two cleanroom standards. Similarly, at least one threshold may comprise a predetermined threshold determined at least in part on at least one facility guideline, a combination of at least two facility guidelines, and/or the like.

Other predetermined thresholds may be determined based upon previous measurements. For example, at least one threshold comprises a predetermined threshold determined at least in part on baseline sensor data. The baseline sensor data may be measured at the facility during a baseline measuring period. Baseline sensor data may also be determined, at least in part, based on open air measurements taken outside the facility.

Yet other predetermined thresholds may be determined based on the location of a sensor. For example, a particle count threshold for a particle counting sensor may be lower for a sensor located in an operating room than for a sensor located in a waiting room.

There can be multiple types of thresholds for various situations, locations, sensors, combinations thereof, and/or the like. At least one threshold may comprise a light threshold. A light threshold may be set with regard to the illumination in a room. One light threshold may be set for evening and another for during the day. Another light threshold may be determined based on the locations, such as, for example, a patient room, an operating room, a hallway, a waiting room, and/or the like.

Thresholds may be set for different levels. In other words, multiple thresholds may be set for the same for a sensor in a particular location. For example, a vibration sensor may have a low, medium and high threshold. Each of these thresholds may be employed by a monitoring system to invoke different actions. A light threshold may alert a nurse. A medium threshold may alert a facility manager. A high threshold may send out an alert to a community monitor.

At least one threshold may comprise a sensor specific threshold. A sensor specific threshold may be set based on the individual characteristics of an individual sensor. For example, it may be determined that a particular temperature sensor has unique non-linear characteristic(s). Specific thresholds associated with this particular sensor may be set to account for the unique non-linear characteristics of the sensor.

At least one threshold may comprise a multiple sensor threshold. A multiple sensor threshold may require that a plurality of conditions occur for a multitude of sensors. Without the plurality of conditions occurring, the threshold will not be met. The plurality of conditions may be as simple as two sensors each exceeding a simple level threshold. The plurality of conditions may be more complex and require a specific sequence of sensor behaviors before activating.

Some thresholds may comprise a time component. A time component may consider, for example, aberrations from an expected rate of change in value(s), the time of day and/or the like. Some thresholds may comprise an occupation component. An occupation component may consider, for example factors that may affect the amount of contamination at a location. (e.g. an increase in the quantity of people (occupation status) increasing the number of contamination particles).

Thresholds may be communicated between environmental sensing devices, environmental monitoring devices, and/or the like. These communications may be, according to some embodiments, caused by processing hardware under the control of machine executable instructions. For example, a machine readable instructions segment of memory on an environmental sensing device may include machine readable instructions configured to cause processing unit(s) to communicate at least one threshold to at least one environmental monitoring device. Similarly, thresholds may be communicated from environmental monitoring device(s) to environmental sensing device(s), between environmental monitoring device(s), and between environmental sensing device(s).

An alarm is a warning indication. The warning indication may be generated by, for example, an environmental monitoring device 370. According to some of the various embodiments, alarm data associated with alarms may be stored in an alarms segment 346 of memory 340. The alarms segment 346 may be stored in a continuous block or may be divided into discrete segments. The discrete segments may be stored in various parts of the memory. Some parts of the alarms segment 346 may be on a disk drive, while other parts may be on a solid state drive. Yet other parts may be stored off device, accessible via communications I/O interface 350. The alarm data may include parameters for the alarms, formulas for setting alarms, alarm events, alarm history, and/or the like.

According to some of the various embodiments, alarm operations may be conducted via machine readable instructions executed via processing unit(s). Some of the operations may be performed on the environmental monitoring device, an environmental sensor device, an external device configured to perform alarm operations (e.g. a SaaS on a server, an external alarm device, a smart device, and/or the like). Some alarm data may be shared among such various devices.

According to some of the various embodiments, processing unit(s) may be employed to set at least one alarm. Alarm(s) may be set according, at least in part, based on a predetermined threshold. For example, an alarm may be set when a value (e.g. sensor value, combinations of sensor values, a sequence of events, and/or the like) exceeds a predetermined threshold. In another example, at least one alarm may be set when a sensor specific threshold is exceeded. In yet another example, at least one alarm may be set when a multitude of sensor thresholds are exceeded.

At least one alarm may be set according to an alarm fatigue rule. Alarm fatigue may occur when one is exposed to a large volume of alarms and, as a result, one becomes desensitized to the firing alarms. Desensitization can lead to longer response times or missing important alarms. The constant sounds of alarms and noises from devices such as blood pressure machines, ventilators and heart monitors may cause a "tuning out" of the sounds due to the brain adjusting to stimulation. This issue is present in hospitals, in home care environments, nursing homes and other medical facilities alike. According to some of the various embodiments, alarm settings may be set to report alarms to specific parties tasked with handling the situation that generated the alarm.

At least one alarm may be categorized as at least one of the following: a data alarm; a network alarm; a calibration alarm; a combination of the above; and/or the like. A data alarm may indicate that one or more sensors are reporting data that has been determined to be out of an expected range. A network alarm may indicate communication problems. Some network alarms may be more important than others. For example, one alarm may indicate the total loss of communications with a device. Another alarm may indicate intermittent communication loss. Yet other network alarms may indicate that only a particular connection is having difficulty. A calibration alarm may indicate that a sensor and/or device may need to be calibrated. Calibration may be schedule based, or determined by observing reading over time. In some cases sensor data may be compared with other sensor data to determine that a device is out of calibration. Some alarms may combine classifications.

According to some of the various embodiments, at least one alarm may be reported to at least one of the following: a facility worker; a network administrator; a healthcare professional; an emergency responder; a combination of the above; and/or the like. A determination as to where an alarm may be routed may be based on an alarm classification. For example, a network alarm may be routed to a network administrator and not reported to a healthcare worker. A data alarm that indicates a probability of harm to a patient (e.g. hazardous gas alarm) may be reported to a healthcare professional and/or an emergency responder in addition to a facility worker and not to a network administrator. Some data alarms may indicate that an air filter is getting dirty. Such an alarm may be reported to a facility worker without involving a healthcare worker.

The reporting of alarms may be performed according to a notification list. For example, if a network alarm goes off, the system may contact a scheduling network administrator and then a network manager and then a network technician sequentially, until the alarm is reset. Each of these parties may be listed on a notification list. The notification list may also include contact information including, but not limited to: a preferred method of notification, a preferred method of notification based on the time of day and week, an alternative method of notification, and/or the like. Methods of notification may include, but are not limited to: email, cell phone, instant messaging, audible (sound) notification, visual notification (e.g. blinking light), combination thereof, and/or the like. Some embodiments may start with the least disturbing methods first (e.g. sounds and lights) when the alarm does not require immediate attention.

Some embodiments may employ an "ignore period" where alarm(s) may be silenced for an alarm specific delay time. Some embodiments may initiate an initial alarm and then implement an "ignore period" before sounding the alarm again. Each time the alarm is sounded, it may be modified to become more noticeable to the appropriate person. According to some embodiments, some alarms may be reset after a reset delay. A reset delay may be a period of time that an alarm is reported. Alarms may be reported to at least one external monitoring device.

Embodiments may generate one or more reports. Alarms may be added to report(s). Alarms and reports may be communicated to at least one other device such as an environmental sensor device, environmental monitoring device, a monitoring program, and/or the like. When the other device receives an alarm, the other device may take additional actions. The additional actions may include, but are not limited to: employing the alarm to set an additional alarm, amplify the alarm as a condition in setting another alarm, relay the alarm, record the alarm, report the alarm, and/or the like. For example, an environmental sensor device may communicate a hazardous gas alarm from a high pressure room to an environmental sensor device in an adjoining lower pressure room. This may cause the environmental sensor device in the adjoining lower pressure room to set off its own hazardous gas alarm ahead of measuring a dangerous hazardous gas level itself. Alternatively, the environmental sensor device in the adjoining lower pressure room may lower a hazardous gas threshold in anticipation that hazardous gas may leak into its location.

According to some of the various embodiments, processing unit(s) may calibrate at least one of the multitude of sensors and/or cause at least one of the multitude of sensors to be calibrated. The calibration may be based, at least in part, on a baseline measurement(s). The baseline measurement(s) may be based on measurements taken at a facility or location in use at an earlier time, in a laboratory/testing facility, and/or the like. The calibration may be based, at least in part, on an absolute measurement. The absolute measurement may be made under conditions where the value of the measurement is known. For example, to calibrate a pressure sensor, a measurement may be made in a chamber that can be set to at least one known pressure, such as one atmosphere, two atmosphere, etc.

Sensor(s) may also be calibrated against a known standard. A standard is an object, system, or experiment that bears a defined relationship to a unit of measurement of a physical quantity. Standards are the fundamental reference for a system of weights and measures, against which all other measuring devices may be compared. Standards may be defined by many different authorities. Many measurements are defined in relationship to internationally-standardized reference objects, which are used under carefully controlled laboratory conditions to define the units of, for example, length, mass, electrical potential, and other physical quantities. Some standards are known as reference standards.

Some calibration may employ a calibration device. A calibration device may be a measurement device that has itself been calibrated and verified. Such a device may have a resolution greater than that required for the sensor being calibrated. Calibration devices may be obtained from companies such as Extech Instruments Corporation of Nashua, N.H. The calibration for at least one of the multitude of sensors may be based, at least in part, by determining and then employing a measurement correction factor between a measurement on a particular sensor and the known quantity being measured.

Embodiments of both environmental sensor device(s) 100 and environmental monitoring device(s) 370 may comprise and/or employ user interfaces. A user interface relates to components and/or systems employed to effectuate human and machine interactions. The interaction communicates operation and control desires of a user and/or feedback from a machine. The user interface may comprise a graphical user interface, at least one switch, at least one indicator, at least one display, at least one touch screen, at least one projector, a combination thereof, and/or the like. According to some of the various embodiments, a user interface may be employed to set and/or report: at least one threshold, at least one alarm, operating parameters, at least one status, and/or the like. A user interface may be configured to display and/or graph data. Data may also be presented as peak data, present peak data, recommended values for at least one threshold, recommended values for alarms, and/or the like. Recommended values for thresholds and/or alarms may be based upon, at least in part, specific sensors, measurements on sensors, calibration data, values from facility guidelines, previous measurements, intended use of a location, values from a standard, and/or the like.

Embodiments of both environmental sensor device(s) 100 and environmental monitoring device(s) 370 may be configured to display reports. Reports may display information such as, but not limited to: real-time raw sensor data, real-time processed sensor data, historical raw sensor data, historical processed sensor data, analyzed data, thresholds, alarms, location, time, calibration data, statistical data, recommended values for alarms, thresholds and/or other parameters, and/or the like. Reports may be configurable or standard. Reports may be based upon templates. Reports may be created on a local device, created on an external device, created using information and/or data from an external device, a combination thereof, and/or the like. Similarly, reports, in part or in whole, may be communicated to an external device and/or received from an external device. In some embodiments, a report may be generated locally based, at least in part, on information and/or configuration data from an external device. Similarly, a report may be generated remotely based, at least in part, on information and/or configuration data from a local device. Reports may be communicated to recipients listed in a notification list. The communication may be via email, text messaging, cellular calls, nurse call tag, pager, intercom, combinations thereof, and/or the like.

According to some of the various embodiments, environmental monitor device 370 may also be configured to collect sensor data from at least one environmental sensor device.

Figure 5:
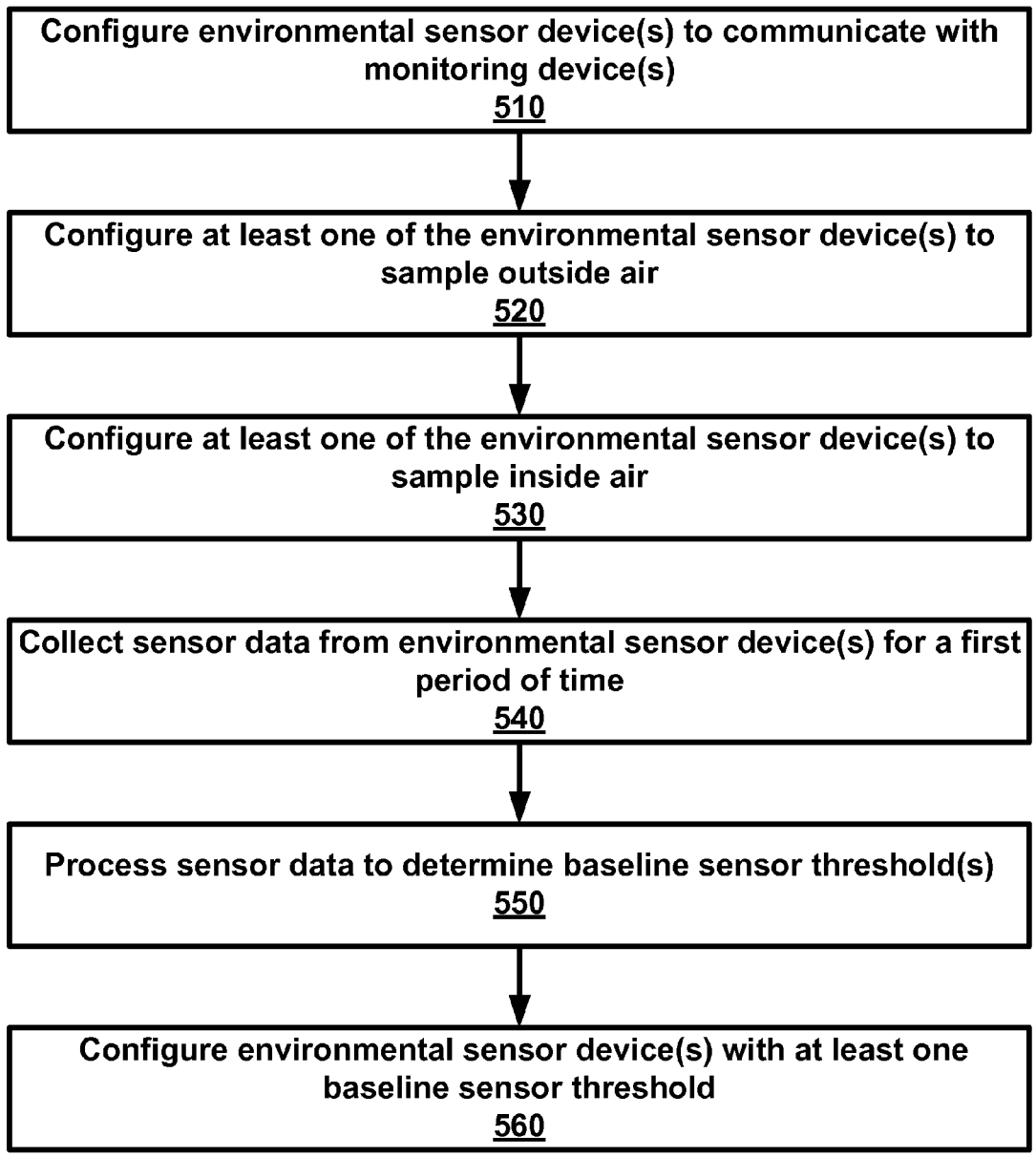
FIG. 5 is a flow diagram illustrating an aspect of an embodiment of the present invention.

Some of the various embodiments may be performed as a method employing environmental sensor devices and/or environmental monitor devices. For example, according to an example embodiment, thresholds may be set by employing one or more of the following actions as illustrated in FIG. 5. A multitude of environmental sensor devices may be configured to communicate with at least one external monitoring device at 510. According to some of the various embodiments, the multitude of environmental sensor devices may comprise: at least one particle counter, at least one differential pressure sensor, a combination of the above, and/or the like. Other sensors may also be employed. Examples of other sensors comprise, but not limited to: a light sensor, a sound sensor, an air-quality sensor, and/or the like.

At 520, at least one of the environmental sensor devices may be configured to sample outside air. At least one of the environmental sensor devices may be configured to sample inside air at 530.

Sensor data may be collected from the multitude of environmental sensor devices for a first period of time at 540.

The sensor data may be processed to determine at least one baseline sensor threshold at 550. The baseline sensor thresholds may be determined by comparing collected sensor data from the outside air to collected sensor data from the inside air. Baseline sensor threshold(s) may also be determined by, for example, comparing collected sensor data with values derived from at least one cleanroom standard, facility guide, air quality standard, combination thereof, and/or the like.

At least one of the multitude of environmental sensor devices may be configured with at least one baseline sensor threshold at 560. For example, at least one alarm is set based, at least in part, on at least baseline sensor threshold. Baseline sensor threshold(s) may be communicated to at least one external device such as, but not limited to: an external environmental monitoring device 170, another environmental sensor device 100, a server, a SaaS, a smart device, a cell phone interface, a web interface, a combination thereof, and/or the like. Further, baseline sensor threshold in a database may be stored in one or more of these various locations. Baseline sensor threshold(s) may be stored in database(s).

Figure 6:
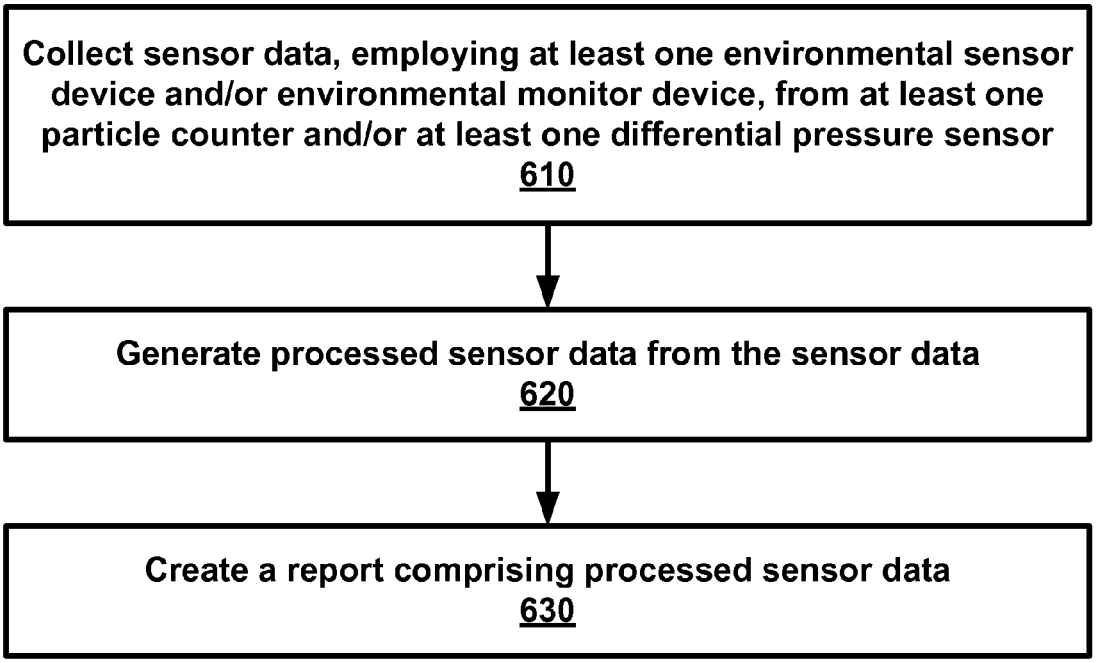
FIG. 6 is a flow diagram illustrating an aspect of an embodiment of the present invention.

Another example embodiment may comprise a method of monitoring environmental air quality as illustrated in FIG. 6. At 610, sensor data may be collected, employing at least one environmental sensor and/or monitoring device from at least one particle counter and/or at least one differential pressure sensor. At 620, processed sensor data may be generated from the sensor data. At 630, a report that comprising processed sensor data that exceeds at least one threshold may be created. The report may be distributed as discussed earlier.

Other embodiments may employ firmware in one or more devices such as, but not limited to: an external environmental monitoring device 170, another environmental sensor device 100, a server, an SaaS, a smart device, a cell phone interface, a web interface, a combination thereof, and/or the like.

Firmware is the combination of persistent memory and program code and data stored in the persistent memory. Persistent memory may include non-transitory storage medium(s). The program code may comprise machine readable instruction configured to cause one or more processors to perform prescribed actions.

Typical examples of devices containing firmware are embedded systems such as: external environmental monitoring devices, environmental monitor devices, computers, computer peripherals, mobile phones, combinations thereof, and/or the like. The firmware contained in these devices may provide the control program for the device.

Firmware may be held in non-volatile memory devices such as ROM, EPROM, or flash memory. Changing the firmware of some devices may be performed during the lifetime of the device; some firmware memory devices may be permanently installed and unchangeable after manufacture. Common reasons for updating firmware include fixing bugs or adding features to the device. This may require ROM integrated circuits to be physically replaced or flash memory to be reprogrammed through a special procedure. Some firmware may provide elementary basic functions of a device and may provide services to higher-level software. Firmware such as the program of an embedded system may be the only program that will run on the system and provide all of its functions. On other devices, the firmware may be augmented with additional machine readable instructions.

Flashing (or flashing firmware) may be employed to overwrite existing firmware or data on memory modules present in an electronic device. This may be done to upgrade a device or to change the provider of a service associated with the function of the device, such as changing from one monitoring and control service provider to another.

According to some embodiments, program code may be employed to cause at least one processing unit in an environmental sensor device and/or environmental monitor device to: collect sensor data from at least one particle counter; generate processed sensor data from the sensor data; and generate a report of processed sensor data that exceeds at least one threshold that accounts for a remote particle count. In yet another embodiment, program code may be employed to cause at least one processing unit in an environmental sensor device and/or environmental monitor device to: collect sensor data from at least one particle counter; generate processed sensor data from the sensor data; and generate a report of processed sensor data that exceeds at least one threshold, the threshold mapping multiple processed sensor data to a singular value, the threshold applying the value to a healthcare standard. According to yet additional embodiments, program code may be employed to cause at least one processing unit in an environmental sensor device and/or environmental monitor device to: perform many of the other tasks described herein.

Multiple environmental sensor devices may be interconnected via a network. The network may interconnect air quality sensor devices via wired and/or wireless communications. Wired communications may employ various interfaces such as, for example, RS-232, RS-422, Ethernet and/or the like. Some of the interfaces may provide both data and power over, for example, a cable. Wireless interfaces may include, but are not limited to: Wi-Fi, 802.11, Bluetooth, cellular, and/or the like.

Traditionally, connecting multiple co-located devices into a common network was difficult to implement if the devices were not specifically designed to be powered and to communicate over a network. Many devices are not network capable, and have analog voltage or current outputs, such as environmental sensors including temperature, humidity, light, sound, and air quality/gas detection. Some devices may be digital in nature, such as a legacy RS-232 interface, but may be revised with additional circuitry to adapt the interface to other interfaces, such as, for example, an Internet Protocol (IP) based network environment. Some devices may be network compatible, but require separate data and power connections per device. For these reasons, connecting a group of devices into a modern IP based network environment may require multiple data connections to be made between the devices and/or a central network, as well as multiple power connections that may require different voltages.

While some applications may support such multiple power and data connections, many applications do not. One such application is interior enclosures used for housing WLAN and telecommunications equipment. In this application, a small number of Ethernet cables are all that may be permissible to connect an equipment enclosure to a network switch, with both data and power required to be carried by the Ethernet cables. An example of how to provide both power and data over an Ethernet cable is provided by IEEE standards that define Ethernet network interfaces (IEEE 802.3), and supplying Power over Ethernet, (IEEE 802.3af/at). So for example, according to some of the various embodiments, a system may be assembled that allows multiple remote stand-alone devices such as environmental sensors with digital or analog outputs, and serial devices such as RS-232 console ports, to be integrated into an 802.3 Ethernet IP based network using an Ethernet connection between the network and remote devices. The devices may communicate with the network and receive power over a single 802.3 Ethernet cable.

Some of the various embodiments of the present invention may be employed to establish environmental thresholds for real-time environmental quality monitoring employing multi-sensor environmental sensor devices. The multisensory environmental sensor devices may be distributed throughout a facility to allow real-time, 24/7 monitoring and long-term profiling. According to some of the various embodiments, the environmental sensor devices may also be moved around a facility as needed to monitor specific areas such as construction or problematic areas.

Environmental sensor devices, environmental monitoring devices and/or environmental systems may be employed in infection control, facilities management, and/or the like. With respect to infection control, some of the various embodiments of the present invention may be employed to, for example: monitor airborne particulate counts facility-wide; monitor differential room pressure of key areas; verify performance protective environment rooms; verify performance of airborne infection isolation rooms; test for elevated humidity levels; and/or the like. With respect to facilities management, some of the various embodiments of the present invention may be employed to, for example: monitor construction and renovation areas for particulates; verify barrier and air filtration effectiveness; monitor indoor air quality (IAQ); verify HVAC performance; generate real-time alerts; and/or the like.

Embodiments of the present invention may be employed to configure, use, and set thresholds for environmental monitoring. For example, embodiments may be employed to: choose metrics on which to set thresholds; create a baseline prior to setting thresholds; establish a methodology for setting thresholds; and/or the like.

Embodiments may monitor a multitude of metrics including, but not limited to: airborne particulates, differential room pressure, air quality, CO2 levels, explosive gas levels, relative humidity, light, sound, vibration, temperature, and/or the like. A default setting may be set for one or more environmental sensor devices to collect data for multiple metrics. Some facilities (e.g. facilities that serve infection control, facilities, and patient satisfaction areas), may be interested in collecting data for all of the metrics. Other applications may desire to set one or more environmental sensor devices to collect data for a subset of metrics.

If a particular metric is of no interest, an environmental sensor device may be set to: not collect data related to that particular metric; disable the display for that particular metric; disable alarms for that metric; disable reporting of that metric; combinations thereof; and/or the like. Settings may be set employing for example: a graphical user interface (GUI); a communications command; a physical switch; combinations thereof, and/or the like. Some embodiments may employ a GUI with an options page that includes for example, a checkbox, to disable all reporting of a particular metric. As with many alarms and thresholds, an options page may be employed to make selections global among multiple environmental sensing/monitoring devices in a facility. Alternatively, options may be performed from an individual environmental sensor device's option page, affecting a single environmental sensor device or a subset of environmental sensor devices.

According to some of the various embodiments, a selection may be made of which metrics may generate alarms. It may be that one or more metrics are of interest from a data gathering perspective, but be of less interest for alarm generation. There may be a balance between needed alarms and alarm fatigue. Alarm fatigue may occur when a user becomes insensitive to alarms due to being overloaded with too many alarms, and in particular alarms which may not be considered critical in nature.

According to some of the various embodiments, in a default installation, room pressure and light may be set to not generate alarms. If the alarm box is checked, any time that the threshold(s) for that metric is (are) exceeded, an alarm will be generated. If the alarm box is not checked, the data for this metric may still be displayed, but no alarms generated, regardless of the data value.

According to some of the various embodiments, a main administrative page may be employed to select which users will be notified when various alarms are activated. Alarms may be "data" alarms, "network" alarms, "calibration" alarms, combinations thereof, and/or the like. "Data" alarms may be generated when a metric exceeds a set threshold. "Network" alarms may be generated when environmental sensor device(s) is/are down, not responding to the server, having network communication issues (e.g. dropped packets), combinations thereof, and/or the like. "Calibration" alarms may be generated when environmental sensor device(s) is/are due for a periodic (e.g. monthly, yearly, etc.) calibration. Alarm fatigue may be mitigated by ensuring that specific staff are assigned to the correct alarm categories.

Averaging of Data.

According to some of the various embodiments, global and/or individual options may be configured to enable one or more metrics to average and/or smooth data. The averaging and/or smoothing operations may employ a range of averaging options. Averaging may be employed to control "noise" and variability of data and to reduce alarms that might be generated on very short term unique events that a user may prefer to ignore. In other words, averaging and/or smoothing may be employed as a tool in controlling alarm fatigue.

By way of example and not limitation, default averaging windows for various conditions may be employed: Airborne Particulates: 20 Minutes; Real-time (R/T) Air Quality: 1 Minute (STEL is fixed at 15 mins, TWA is fixed at 8 hrs); Differential Room Pressure: 1 Minute; Relative Humidity: 10 Minutes; Sound: 10 Minutes; and Light: 10 Minutes. These averaging windows may be changed as needed by the user to obtain a slower response (increased averaging) or a faster response (decreased averaging).

When graphing and exporting data, either the averaging windows set on a threshold page may be used or different averaging windows may be selected as desired for the purposes of graphing and exporting. According to some of the various embodiments, regardless of the averaging window chosen, when graphing, selecting a real time button may be configured to add real time, non-averaged data to a graph for comparison purposes and to give a visual indication of the amount of averaging selected.

When first baselining a facility, a user may try multiple averaging values to achieve a desired response time to unusual or hazardous events, while minimizing false alarms and ignoring short transient events. Selecting an averaging value which is a compromise between too fast of a response and too slow of a response may be made based on the trials. Additionally, according to some of the various embodiments, averaging value(s) may be independently chosen for each metric. Some metrics such as airborne particulates may benefit from increased averaging to ensure an accurate representation of a room, while other metrics such as room pressure may utilize decreased averaging in order to respond quickly to a loss in room pressure.

FIG. 7 is an example GUI 721 configured to set global and/or threshold options and setting. As illustrated, this example GUI 721 may be employed to enable a user to set global options such as, for example, which metrics to display, which metrics to alarm on, and the thresholds for alarm(s). Selections made on a global options page may be applied to multiple environmental sensor devices. A similar options page may be employed for individual environmental sensor devices or subsets of environmental sensor devices, to allow the user to set thresholds differently on a per environmental sensor devices basis.

Initial Threshold Setting Considerations.

According to some of the various embodiments, one example methodology in setting alarm thresholds may be to first baseline a facility. The baseline data may be employed in setting thresholds. In this case, alarm box(es) may be deselected during a baselining period. Apply this setting to environmental sensor devices and operate the environmental sensor devices for an initial baseline period of time. The baseline period of time may be, for example, from a day to as long as a week or more. The baseline period of time may be set to cover a period of time that accounts for a set of normal operating tasks for the facility to be performed, a period that would allow contaminates to move about in a facility, combinations thereof, and/or the like. Data may be collected throughout this baseline period of time. The baseline may be re-visited over time, perhaps, for example, quarterly or yearly. As data is being collected, values for various metrics may be reviewed using, for example, graphing functions to see both daily and long term trends and issues. Once a facility has operated at a normal and acceptable state during the baseline period and baseline data has been collected, thresholds that are slightly more tolerant than the worst case baseline values may be selected and set. This may allow users to be alerted if conditions in the facility deviate from this baseline.

According to some of the various embodiments, another example methodology in setting alarm thresholds may be to set thresholds per recommendations from international or U.S. based standards organizations, such as the ISO (International Standards Organization), OSHA (United Stated Occupational Safety and Health Administration), the FGI/AIA (Facilities Guidelines Institute/American Institute of Architects), and ANSI/ASHRAE/ASHE (American National Standard Institute/American Society of Heating, Refrigeration and Air-Conditioning Engineers/American Society for Healthcare Engineering), combinations thereof, and/or the like.

Examples of metrics that may have thresholds based on standards organizations are airborne particulates, differential room pressure, air quality/CO2, and humidity.

Airborne Particulate Measurements.

According to some of the various embodiments, airborne particulate count(s) may be a metric for infection control but may create a challenge in determining acceptable levels. This section provides information on how to set thresholds for a particulate count according to some of the various embodiments.

Some particle counters in environmental sensor devices may count airborne particulates in multiple channels for particles of different sizes, such as, for example, in four channels of particles of sizes: 0.5 um, 1 um, 5 um, 10 um, and/or the like. Counts may be referenced to particles per cubic feet, particles per cubic meter, particles per liter, and/or the like. Additionally, counts may be reported in various modes such as a cumulative mode, a differential mode, and/or the like.

Some particle counters in environmental sensor devices may count the absolute number of airborne particulates from, for example, 0.5 um to 10 um. There are cleanroom classifications for airborne particulates that are absolute in nature, as well as FGI/AIA guidelines that are relative in nature. Before global cleanroom classifications and standards were adopted by the ISO, the U.S. General Service Administration's standards (US FED STD 209E) were often applied. As the need for international standards grew, the ISO established a technical committee and several working groups to establish its own set of standards, now known as ISO 14644-1.

Some cleanroom standards were developed for applications where an absolute contamination level may be important, such as semiconductor processing and pharmaceutical manufacturing. This same concern with absolute levels of contamination may also have applications to infection control in healthcare institutions, such as preventing infections during surgical procedures or preventing infections within immune compromised patient communities.

Examples of cleanroom standards include: ISO 14644-1, which contains 9 classes; ISO 1 through ISO 9; FED STD 209E, which contains 6 classes, and Class 1 through Class 100,000. The charts in FIG. 8A and FIG. 8B show both ISO 14644-1 and FED STD 209E standards for comparison. These measurements are in a cumulative mode and are absolute in nature. These standards are presented for illustrative purposes. Those skilled in the art will recognize that other requirements could be applied to various embodiments.

ISO standard created for semiconductor clean rooms may be adapted to be used with particle counters in a healthcare environment. For example, a subset of ISO classes applicable to healthcare facilities may be identified. In addition to the sub-set, larger particle size limits may be extrapolated and applied to a class. Raw data from multiple channels of a particle counter may be reduced to a single class value. Processing may keep track of the number of particles counted in each bin over an averaging period and ignore bins where the particle count is very low (to minimize measurement uncertainty).

In comparison to the absolute international and U.S. cleanroom standards, the FGI/AIA ANSI/ASHRAE/ASHE 170/2010 Design Guideline recommendations may also be applied to various embodiments as recited in the following illustrative relative requirements: Protective Environment: High Efficiency Particulate Air (HEPA) (99.97% removal of 0.3 um and greater particles); Class B, C Surgery, Inpatient Care, Treatment, Diagnosis: MERV 14 (85% removal of 0.3 um, 90% removal of 1 um and greater particles); Class A Surgery, Laboratories: MERV 13 (75% removal of 0.3 um, 90% removal of 1 um and greater particles); Nursing Facility: MERV 13 (75% removal of 0.3 um, 90% removal of 1 um and greater particles); Inpatient Hospice Facility: MERV 13 (75% removal of 0.3 um, 90% removal of 1 um and greater particles); and Assisted Living Facility: MERV 7 (70% removal of 1 um and greater particles). It should be noted that these requirements may be relative to a facility fresh outside air intake particulate level. High Efficiency Particulate Air (HEPA) filters may be assigned MERVs based on their performance in accordance with standards published by the IEST (Institute of Environmental Sciences and Technology). Minimum Efficiency Reporting Value (MERV) may be a measure used to describe the efficiency with which particulate filters remove particles of a specified size from an air stream.

There are also several European health care airborne particulate standards that may be employed, some of which may be more thorough than the US standards, in that they consider differences between a room at rest (unoccupied) and in use (occupied as intended).

At rest measurements may be useful to determine how well a basic facility air filtration system is performing. In use measurements may be useful to determine how well the room ventilation design is performing at keeping particulates generated by personnel and their movement from entering the protected area located around the patient. In any given operating room, for example, the design of the ventilation system may be such that filtered air is allowed to flow directly down onto the patient, and then wash away from the patient, and eventually be directed into return ducts outside a protected area surrounding the patient. In this manner, particulates generated by personnel should not enter the protected area and instead should be directed into return ducts.

Another example standard, German standard DIN 1946-4: 2008-12, requires an at rest limit of class H13 HEPA filter (ISO 5) in Class 1 rooms, and also specifies a degree of protection during occupied times of at least 2.0 if surgical lights are present, and at least 4.0 if no surgical lights are present. A degree of protection of 2.0 may be equivalent to ISO 7, and a degree of protection of 4.0 may be equivalent to ISO 5. Yet other example standards, French standard NF S 90-351:2003-06 and Italian standard UNI 11425:2011-09 both place limits on airborne particulates in an at rest situation at ISO 5.

Setting Airborne Particulate Thresholds.

The FGI/AIA standards may be relative, requiring a certain percentage reduction with respect to the actual outdoor environment. Sampling the outdoor environment, it may be possible to baseline and continuously monitor the outdoor environment and set thresholds which vary based upon the outdoor environment.

However, according to an alternative embodiment, thresholds may be set low enough for fixed absolute limits for healthcare facilities, based upon worldwide cleanroom standards, and a worldwide definition of nominal outdoor urban air quality, which is ISO 9.

Rather than monitoring multiple size channels and setting individual limits per channel, particle counters in environmental sensor devices may categorize airborne particulates in terms of compliance to a standard such as, for example, an absolute ISO class based standard. In such example embodiments, particle counters in environmental sensor devices may be configured to, for example, measure particles from 0.5 um to 10 um, and spans the ISO cleanroom standards, as well as the FGI/AIA standards, and employ extrapolated ISO based limits for a 10 um channel. FIG. 8B is a table of an example ISO Class limits that may be employed to set thresholds for categories of measured particle.

Assuming that the outside air quality is equivalent to ISO 9/Urban Air as the reference point for the FGI/AIA requirements, it may be possible to map these relative requirements into absolute limits. Using this methodology to set limits may require facilities located where the outside air is dirty to provide additional filtering to achieve an indoor particulate level that is as low as a facility located where the outside air quality is equivalent to or better than ISO 9/Urban Air. Using, for example, ISO 9 as a fixed reference, each ISO level may represent the following relative reductions in particulate levels: ISO 9 Reference: 100%; ISO 8: 90%; ISO 7: 99%; ISO 6: 99.9%; ISO 5: 99.99%; ISO 4: 99.999%; and ISO 3: 99.9999%.

Using, for example. limits specified in the FGI/AIA standards, requirements may be mapped into the following example ISO levels: a HEPA limit of 99.97% removal based upon ISO 9 as a reference may result in using an ISO 5 limit (99.99%); and a MERV 13/14 limit of 90% removal based upon ISO 9 as a reference may result in using an ISO 8 limit (90%).

According to some of the various embodiments, using the ISO class limits such as described above, an ISO class alarm mode may be employed with the ISO class alarm thresholds set as follows: Protective Environments—ISO Class 5 (at rest), ISO Class 5.5 to 6 (in use); Class B, C Surgery—ISO Class 5 (at rest), ISO Class 5.5 to 6 (in use, invasive implant procedures), ISO Class 6 to 7 (in use, general procedures); Class A Surgery, Inpatient Care, Treatment, Diagnosis, Laboratories—ISO Class 8 (in use); Nursing Facility; ISO Class 8; Inpatient Hospice Facility—ISO Class 8 (in use); Assisted Living Facility—ISO Class 8 (in use); and other location requiring tight control—ISO Class 6-7 (in use). Of course, embodiments may provide an option to choose to not use an ISO Class of airborne particulate thresholds. Custom limits may be set in particle count size bins such as the 0.5 um, 1 um, 5 um, and 10 um sized bins. Additionally, thresholds may be calculated in either a cumulative and/or differential mode.

ISO based measurements may be inherently made in a cumulative mode. A cumulative counting mode may include all particles that are equal or greater to a channel size. For example, if a 7 um particle is counted, it may yield one count in each of the 0.5 um, 1 um, and 5 um channels, and a zero count in the 10 um channel.

A differential counting mode may include particles that are equal or greater than a channel size, but less than the next greater channel size. For example, if a 7 um particle is counted, it may yield a zero in the 0.5 um and 1 um channels, a 1 in the 5 um channel, and a zero in the 10 um channel.

A default mode of operation may be an ISO Class 8 mode operating in a cumulative mode of operation.

In any given facility, it may be desirable to set environmental sensor device thresholds separately. For example, an operating room may require lower thresholds and a construction area or general treatment room may have higher thresholds. One may employ a global threshold setting to set all units to the most commonly used thresholds and then individually (or in subgroups) adjust environmental sensor units as needed.

The airborne particulate sensor may normally operate with approximately a 50% duty cycle, (e.g. one minute on and one minute off) to allow for precise sound measurements to be made during the off cycle. In environments such as operating rooms, if a noise measurement is not needed, the particulate pump may be set to run more often (e.g. always run), which may decrease the measurement uncertainty of the particulate measurement.

The particulate pump may be set to off, which in turn may disable airborne particulate measurements and improve the accuracy of the sound measurement. By way of example, and not limitation, available pump modes may be set to: 50% duty cycle (default), always on (sound measurement disabled), and always off (airborne particulate measurement disabled).

Differential Room Pressure Thresholds.

Certain rooms within a healthcare institution may be pressurized, either positively or negatively. Examples of positively pressurized rooms are operating room (OR) and protective environment (PE) rooms. Examples of negatively pressurized rooms are airborne infection isolation (AII) rooms and construction areas.

The FGI/AIA ANSI/ASHRAE/ASHE 170/2014 Guidelines list the following differential pressure limits for various environments: AII Rooms: Negative 2.5 Pa/0.01 in WC; Bronchoscopy Procedure/Sputum Induction Rooms: Negative 2.5 Pa/0.01 in WC; PE Rooms: Positive 2.5 Pa/0.01 in WC; Class B/C OR Rooms, Operating/Surgical Cystoscopic Rooms, Caesarean Rooms: Positive 2.5 Pa/0.01 in WC and Hospital Construction Barriers: Negative 7 Pa/0.03 in WC. Similarly, the CDC (Centers for Disease Control and Prevention) EIC MMWR list the following differential pressure limits for various environments: PE Rooms: >Positive 8 Pa; and AII Rooms: <Negative 2.5 Pa. Some embodiments may be configured to test environments for pressure on an on-going basis where pressurization may be maintained on an on-going basis.

For rooms requiring differential room pressure to be maintained, alarm threshold may be set. For example, a differential room pressure alarm threshold may be set to at least 5 Pa in general; and at least 8 Pa for PE rooms and construction barriers. Either a negative or positive threshold may be selected as appropriate.

Thresholds for differential pressure may be very small and difficult to measure. Pressure sensors may come calibrated from the factory, but differences in physical orientation (horizontal on a desk/cart versus vertical in the wall mount bracket) and shifts due to physical shipping and handling may cause the zero point of the sensor to shift slightly. While this shift may be small with respect to the limits above, it may be advantageous that pressure sensors used for pressure measurement be re-zeroed at times such as: after a final installation, after a move, after a construction event, and/or the like. This may, according to some embodiments be executed from an individual unit's options page.

Air Quality/$CO_2$ Thresholds.

Although normal levels of $CO_2$ may be considered harmless, under the right conditions $CO_2$ may cause adverse health effects. High concentrations of $CO_2$ in confined areas may be potentially dangerous. $CO_2$ may act as an oxygen displacer in confined spaces and cause a number of reactions. These reactions include, but are not limited to: dizziness, disorientation, suffocation, and under certain circumstances, death. CO2 may be measured in terms of parts per million (ppm), by volume of air.

CO2 may be a good indicator of proper building ventilation and indoor air exchange rates. CO2 may be measured in buildings to determine if the indoor air is adequate for humans to occupy the building.

The following may occur as a symptom from differing concentrations of CO2: 2,000 ppm—shortness of breath, deep breathing; 5,000 ppm—breathing becomes heavy, sweating, pulse quickens; 7,500 ppm—headaches, dizziness, restlessness, breathlessness, increased heart rate and blood pressure, visual distortion; 10,000 ppm—impaired hearing, nausea, vomiting, loss of consciousness; and 30,000 ppm—coma, convulsions, death.

According to some of the various embodiments, an environmental sensing unit may report CO2 multiple ways, such as, but not limited to: Real-Time (R-T), Short Term Exposure Limit (STEL), and Time Weighted Average (TWA). These three example CO2 measurements differ, in part, by how long the measurement is integrated over time. For example R-T results may be integrated over approximately several seconds (e.g. 5-15 seconds), STEL measurements may be integrated over approximately several minutes (e.g. 5-15 minutes), and TWA results may be integrated over approximately several hours (e.g. 5-12 hours).

Thresholds may be set according to suggested limits. For example, thresholds may be set according to OSHA suggested limits. OSHA has set the following permissible exposure limits (PEL) for occupied buildings: STEL—30,000 ppm; and TWA—5,000 ppm. Default thresholds may be set at various values, such as, but not limited to: R-T—1,250 ppm; STEL—1,250 ppm; and TWA—1,250 ppm. According to some embodiments, CO2 (or other gas) thresholds may be changed or not selected for alarm, as deemed appropriate.

Relative Humidity Thresholds.

According to some of the various embodiments, humidity sensor(s) may be employed in environmental sensing devices to measure humidity. Guidelines may be employed to set relative humidity thresholds. For example, FGI/AIA ANSI/ASHRAE/ASHE 170/2014 Guidelines suggest the following relative humidity limits be maintained: Critical and Intensive Care—30-60%; Endoscopy Procedure Rooms—30-60%; Class B/C Operating Rooms—20-60%; Treatment/Recovery Rooms—20-60%; and PE/AII Rooms—Max 60%. Default relative humidity thresholds may be set to 30-60%. According to some embodiments, relative humidity thresholds may be changed or not selected for alarm, as deemed appropriate. When some embodiments are first powered on, a delay in the measurement and reporting of relative humidity may be implemented to allow humidity sensor(s) to stabilize. For example, some embodiments may employ a delay in the range of 10 to 40 minutes to allow humidity measurement(s) to stabilize.

Light Thresholds.

According to some of the various embodiments, ambient light sensor(s) may be employed in environmental sensing devices. According to some embodiments, ambient light sensor(s) may be provided that approximate the human eye response to visible light. Rejection to infrared and 50/60 Hz lighting ripple may also be provided. The light level may be displayed as Lux. A light sensor input port may be located in a position visible to light in an environment. For example, the light sensor may be disposed on the top of an environmental sensing device. Some embodiments may allow the light sensor to be positioned to face a main desired source of light for satisfactory operation.

An alarm may be set for a desired light level, configurable for both low light or high light thresholds. A default setting is an alarm associated with a light sensor that may be disabled, with limits such as, for example, approximately 200 Lux and/or 2000 Lux. According to some embodiments, light thresholds may be changed or not selected for alarm, as deemed appropriate.

Sound Thresholds.

According to some of the various embodiments, audio sound sensor(s) may be employed in environmental sensing devices. Audio sound sensor(s) may be configured with, for example, a wide dynamic range logarithmic amplifier and/or an A-weighted audio filter to approximate the human ear response to different sound frequencies. The audio level may be displayed/reported as dB (decibel) sound pressure level, A-weighted (dBA SPL).

Audio sound sensor(s) may be used to provide a quantitative baseline of the noise level within a healthcare environment. Normal speaking voices may be approximately 65 dBA. Levels above 85 dBA may permanently damage hearing. The NIOSH (National Institute for Occupational Safety and Health) has established a permissible exposure time of 8 hours at a level of 85 dBA SPL.

By way of example, and not limitation, the FGI/AIA ANSI/ASHRAE/ASHE 170/2014 guidelines may be employed in setting sound thresholds. For example, the following sound guidelines may, according to some of the various embodiments, be employed: separate limits be set for day and night periods; the night limit be set 5 to 10 dBA below the day limit; and daytime limits may typically vary between 55 and 65 dBA.

An alarm may be set for a maximum sound level desired. According to some of the various embodiments, a default sound threshold may be set at 80 dBA SPL. According to some embodiments, sound threshold(s) may be changed or not selected for alarm, as deemed appropriate.

When airborne particulates are also measured, sound measurement(s) may be de-sensitized during the airborne particulate pump cycle. This pump may be set to off to disable airborne particulate measurements and improve the accuracy of the sound measurement. Example available pump modes may comprise: 50% duty cycle (default), always on (sound measurement disabled), and always off (airborne particulate measurement disabled).

Differential Pressure.

Some of the various embodiments may employ pressure sensor(s) such as a differential pressure sensor, a single pressure sensor or a multitude of pressure sensors.

A differential pressure sensor within an environmental sensing unit may be configured to measure the pressure differential between the ambient pressure in the room in which the sensor is installed (the reference location) and an adjacent room or hallway (the external location). According to some embodiments, both positive and negative pressure differentials may be measured. Pressure may be displayed/reported in, for example, Pascal (Pa), with a full scale of approximately +/−24.9 Pa.

In embodiments in which both positive and negative differential pressure may be measured, measurement polarit(ies) may need to be observed. Some rooms may be configured to be positively pressurized (the room pressure is greater than the adjacent room or hallway) or negatively pressurized (the room pressure is less than the adjacent room or hallway).

A reference port may be inside an embodiment of an environmental sensing unit. A measured external port may be located on an outside (e.g. rear) panel. A quick disconnect fitting may be employed to simplify this connection. A tube may be routed from the external port to an adjacent room or hallway. Various static probes and wall plates may be employed to complete this connection.

The differential pressure sensor may be a precision device, configured to measure small pressure differentials. The zero pressure point may be factory calibrated, however changes in physical installations of an environmental sensor unit embodiment may cause small shifts in this zero pressure calibration. According to some of the various embodiments, environmental sensor device firmware may be employed to re-zero the zero pressure state. The environmental sensor device firmware may zero the zero pressure state in response to a command. The command may be internal or may be initiated from an external monitoring device and/or other control system. The environmental sensor device may be stationary when performing a zero pressure calibration. The environmental sensor device may be in mounted position stationary when performing a zero pressure calibration. The mounted position may be a final mounted position. The environmental sensor device may have the external port disconnected with little or no airflow over or around this external port when performing a zero pressure calibration. A default calibration may be stored for retrieval. The default calibration may be a factory calibration.

According to some embodiments, a differential pressure threshold(s) can be set for a desired minimum room pressure. A differential pressure alarm may be changed or not selected for alarm, as deemed appropriate.

Differential Room Pressure Monitoring.

According to several of the embodiments, a variety of accessories may be employed with an environmental sensor device including, but not limited to: quick disconnect fitting(s), wall plate(s), static pressure sensor(s), quick disconnect fitting(s), combinations thereof, and/or the like. Quick disconnect fitting(s) may include an adaptor configured to plug into an external pressure port of an environmental sensor device to allow a user to monitor differential pressure in remote locations. A quick disconnect fitting may be attached, by use of flexible tubing, to, for example: a wall plate, a static pressure sensor probe, combinations thereof, and/or the like.

Room static pressure sensor(s) may be installed in a remote location such as, but not limited to: an external room, a nearby room, a nearby hallway (e.g. adjacent to the location of the remote sensing device), and/or the like. Room static pressure sensor(s) may be installed in a remote location to monitor the pressure differential between the remote sensing device location and the remote location. The room static pressure sensor may be attached to the quick disconnect fitting using flexible tubing. The tubing may be attached to the back side of a wall plate by installing the tubing over a barbed connector adaptor. Alternative configurations may be employed which do not employ quick disconnect fittings.

Static pressure sensor(s) may be installed, for example, through a wall between the location of a remote sensing device and an external room or hallway. Static pressure sensor(s) may, according to some embodiments, be attached to a quick disconnect fitting using flexible tubing. The tubing may be attached to the static pressure sensor by installing the tubing over a barbed adaptor. Static pressure sensor(s) with various lengths may be employed to match varying wall thicknesses, such as, for example, 4", 6", 8", and/or the like.

Tubing may be installed to a quick disconnect adaptor by aligning the end of the tubing with the barbed end of a quick disconnect adaptor. The tubing may be pressed firmly in place until it reached the flange of the adaptor. The tubing may be gently pulled to verify that it is locked in place.

A static pressure sensor may be installed in a wall as follows. Determine a size based on the thickness of the wall where the sensor will be placed. Determine a proper location to create a wall penetration. Verify that there are no utilities located between the layers of wall board in the desired location including: electrical cabling, water pipes, duct work, networking equipment, etc. Drill a hole through the wall, including wall board or other wall material on each side of the wall. Insert the static pressure sensor through the drilled hole. Verify that the end of the static pressure sensor extends fully through the hole and into the area where external differential pressure is to be measured. Secure the static pressure sensor in place using screws or other sufficient attachment mechanism. (e.g. caulk, glue, nails, etc.). Connect tubing to the end of the static pressure sensor. Gently pull the tubing to verify it is in place. If the static pressure sensor probe is too long, an installer may cut the end to make it flush with the outer wall surface. The tubing may be affixed to the environmental sensing device external pressure sensor port.

A static pressure sensor may be installed in a room. A room static pressure sensor may be employed to monitor pressure remotely using an aesthetic wall plate assembly. The room static pressure sensor may be installed in the same manner as a typical wall outlet. A proper location in the room to monitor external pressure may be determined. A standard electric outlet box may be mounted in a wall near the determined location. The tubing from an environmental remote sensing device may be run to the room in the same manner as an electrical or data cable. It may be advantageous to verify that all local codes are being met when performing this type installation. A non-kinking tube adaptor which allows a tube to bend at angles without restricting the air flow through the tubing may be employed to connect the room static pressure sensor to an environmental sensing device. This is useful when working in tight spaces as is sometimes required when installing in an outlet box. The non-kinking tube adaptor may be aligned with a connector on the back of the room static pressure sensor. In some embodiments the room static pressure sensor may employ a barbed connector. In this case, the adaptor may be pressed firmly in place seating against the base of the barbed connector. The tube that was previously run through the wall outlet box to the tube adaptor may be attached to the non-kinking tube adaptor. The wall plate may be attached to the wall outlet box using screws or other attachment mechanisms such as caulk, glue, nails, etc. The room static pressure sensor may be installed in the outlet box. It may be helpful to have as much of the bend in the tubing take place in the non-kinking tube adaptor. The external pressure sensor may then be connected to the tube. Some embodiments may employ a quick disconnect fitting on the back of an environmental sensing device. To install a quick disconnect fitting, (1) depress a latch on the differential pressure sensor connector and then (2) insert the quick disconnect fitting until it snaps on place. Gently pull on the quick disconnect fitting to verify it is properly latched in place.

Some of the various embodiments of the present invention may be employed for healthcare environmental air quality monitoring. Embodiments may be configured for real-time environmental quality monitoring solution, comprised of facility-wide, low-cost, compact, multi-sensor modules. Environmental sensor devices may be placed just about anywhere in the facility to allow immediate real-time and 24/7 monitoring and long-term profiling. Environmental sensor devices may also be conveniently moved around a facility as needed to respond to construction or problematic areas. Multiple environmental sensor devices may be deployed within a facility to ensure adequate coverage.

Environmental sensor devices may assist in infection control by: monitoring airborne particulate counts facility-wide; monitoring differential room pressure of key areas of a facility; verifying performance protective environment rooms; verifying performance of airborne infection isolation rooms; and testing for elevated humidity levels. Environmental sensor devices may assist in facilities management by: monitoring construction and renovation areas for particulates; verifying barrier and air filtration, effectiveness; monitoring indoor air quality (IAQ); verifying performance of HVAC; and generating real-time alerts. Specifically, embodiments of the present embodiment may be configured to: monitor an AII; monitor an AII room with an antechamber; monitor a PE; monitor a PE with an antechamber; monitor a construction area; monitor a combinations thereof, and/or the like.

Environmental sensor devices may be employed to monitor healthcare facilities for compliance with various healthcare facility guidelines. FIG. 9A and FIG. 9B are example healthcare facility guidelines. FIG. 9A is a chart for engineered specifications for positive and negative pressure rooms from the CDC (CDC EIC MMWR Jun. 6, 2003). In FIG. 9A: (1) 1 DOP is an abbreviation for dioctylphthaltate particles of 0.3 um; (2) If the patient requires both PE and AII, return air may be HEPA filtered or otherwise exhausted to the outside; and (3) HEPA filtration of exhaust air from AII rooms may not be required providing that the exhaust is located to prevent re-entry into the building. FIG. 9B is a chart showing example guidelines for design and construction of ORs in healthcare facilities. In addition, the FGI and ASHRAE design guidelines recommend the following: sealed room with about 0.1 cfm/ft2; greater than 125 cfm airflow differential supply vs. exhaust clean to dirty airflow; monitoring of PEs, AIIs, construction and renovation areas, other critical areas; greater than 12 air changes per hour (ACH) in new construction and 6 air changes per hour in renovation areas; and anteroom airflow patterns suitably designed for the application.

Thoughtful placement of environmental sensor devices may assist in accurate monitoring of a facility environment.

Some of the various embodiments of the present invention may be employed to monitor outdoor air quality. Outdoor air quality monitoring may be employed to: create an air quality baseline, verify that indoor air quality is cleaner than outdoor air; monitor for poor outside air conditions; verify differential air pressure; combinations thereof; and/or the like. Outdoor air quality may be adversely affected by dust storms, pollen, outdoor construction, pollution, forest fires, and/or other factors. Before reacting to degraded indoor air quality, it may be useful to know if such degradation is caused by degraded outdoor air quality and particle count. According to some of the various embodiments, environmental sensor device(s) may be located indoors in the proximity of an outdoor location to be sampled. If it is desired to get differential air pressure, environmental sensor device(s) may be located in a nominal air pressure indoor location. Tubing may be conducted from an environmental sensor device's particle detector inlet to the outdoor location. The outdoor location may be located in the proximity of the facility air intake to sample air being brought into the building. A factor may be that the indoor air quality (particle count) is better than the outdoor air quality (particle count), but this is not always the case. It may be desirable (although not always the case), that the indoor air pressure is positive relative to outdoor air pressure.

Some of the various embodiments of the present invention may be employed to monitor AII rooms. AIIs may be designed to protect healthcare workers, other patients, and the public in the hospital environment from potential infection by airborne agents carried by infected, or potentially infected, patients or groups. AIIs may have a negative pressure relative to adjacent spaces, and the (potentially infectious) air inside the AII must be suitably exhausted. With the AII, environmental sensor device(s) may be mounted outside of the AII room so that it can be visually checked without entering the AII (in general, the environmental sensor device(s) may be placed in the positive pressure location). Static sensor pressure tips may be employed to sample the air pressure in the AII, so that the air pressure in the AII may be compared to the air pressure in the adjacent corridor. Thresholds may be set to alert personnel when the differential air pressure drops below desired levels.

An AII anteroom may be used in certain circumstances to provide additional AII capacity in a hospital. In this case, environmental sensor device(s) may be placed in the anteroom, on the wall outside of the AII room. Static sensor pressure tips may be employed to sample the air pressure in the AII room, so that the air pressure in the AII room may be compared to the air pressure in the ante room. The AII room may remain at a negative pressure relative to the anteroom. Thresholds may be set to alert personnel when the differential air pressure drops below desired levels.

Some of the various embodiments of the present invention may be employed to monitor PEs. PEs may be designed to protect patients who are most susceptible to airborne infectious agents. A PE may have a positive pressure relative to adjacent spaces to keep airborne particles from leaking into the PE. With the PE, the environmental sensor device(s) may be mounted inside the PE room so that it may be visually checked periodically by those within the PE. Static sensor pressure tips may be employed to sample the air pressure in the adjacent space, so that the air pressure in the adjacent space may be compared to the air pressure in the PE. Thresholds may be set to alert personnel when the differential air pressure drops below desired levels. In general, the environmental sensor device(s) may be placed in the positive pressure location.

A PE anteroom may be used in certain circumstances to provide additional PE capacity in a hospital. In this case, the environmental sensor device(s) may be placed in the PE room adjacent to the anteroom. Static Sensor Pressure Tips may be employed to sample the air pressure in the ante room, so that the air pressure in the ante room may be compared to the air pressure in the PE room. The PE room may remain at a positive pressure relative to the anteroom. Thresholds may be set to alert personnel when the differential air pressure drops below desired levels.

Some of the various embodiments of the environmental sensor device(s) may also measure particle counts in PE rooms (and other rooms where it is desired to monitor presence or generation of particles). Environmental sensor device(s) may be located close to the diffuser or source of air, high on a wall or ceiling, so that the particle count is representative of the air coming into the room. This may enable the environmental sensor device(s) to detect degradations of incoming air quality and help to minimize "false alarms" due to normal activities within the room which may create spikes in particle counts. In general, the environmental sensor device(s) may be placed in the positive pressure location.

According to some of the various embodiments, environmental sensor device(s) may also be employed to monitor room humidity, which is a requirement in ORs. Sound and light levels can also be monitored which are important factors for overall patient satisfaction.

Some of the various embodiments of the present invention may be employed to monitor air quality in construction and renovation areas. Construction and renovation activities may create special requirements for monitoring differential pressure and particle counts. Work areas within a hospital may be maintained at a negative pressure so that particles generated within the work area do not spread through the facility. The air within the work area may be circulated through a HEPA filter and is exhausted.

Environmental sensor device(s) may be located outside of the work area. Static sensor pressure tips may be employed to sample the air pressure in the work area, so that air pressure in the work area may be compared to the air pressure in the adjacent corridor or patient area. Thresholds may be set to alert personnel when the differential air pressure drops below desired levels, which may indicate that the barrier has been incorrectly constructed, breached or damaged. For soft barriers, environmental sensor device(s) may be mounted on a ceiling adjacent to the barrier, and the sampling tube conducted and attached to the barrier.

Monitoring particle count in areas adjacent to work areas may be employed to detect large increase in particle count caused by construction or renovation, which may signal a degradation in the barrier, malfunction of HEPA filter or fan, or infection control risk assessment (ICRA) procedure violations. Environmental sensor device(s) may be mounted on the ceiling or on a high wall to avoid spurious false alarms due to normal activities, which can create spikes in particle count.

Figure 10:
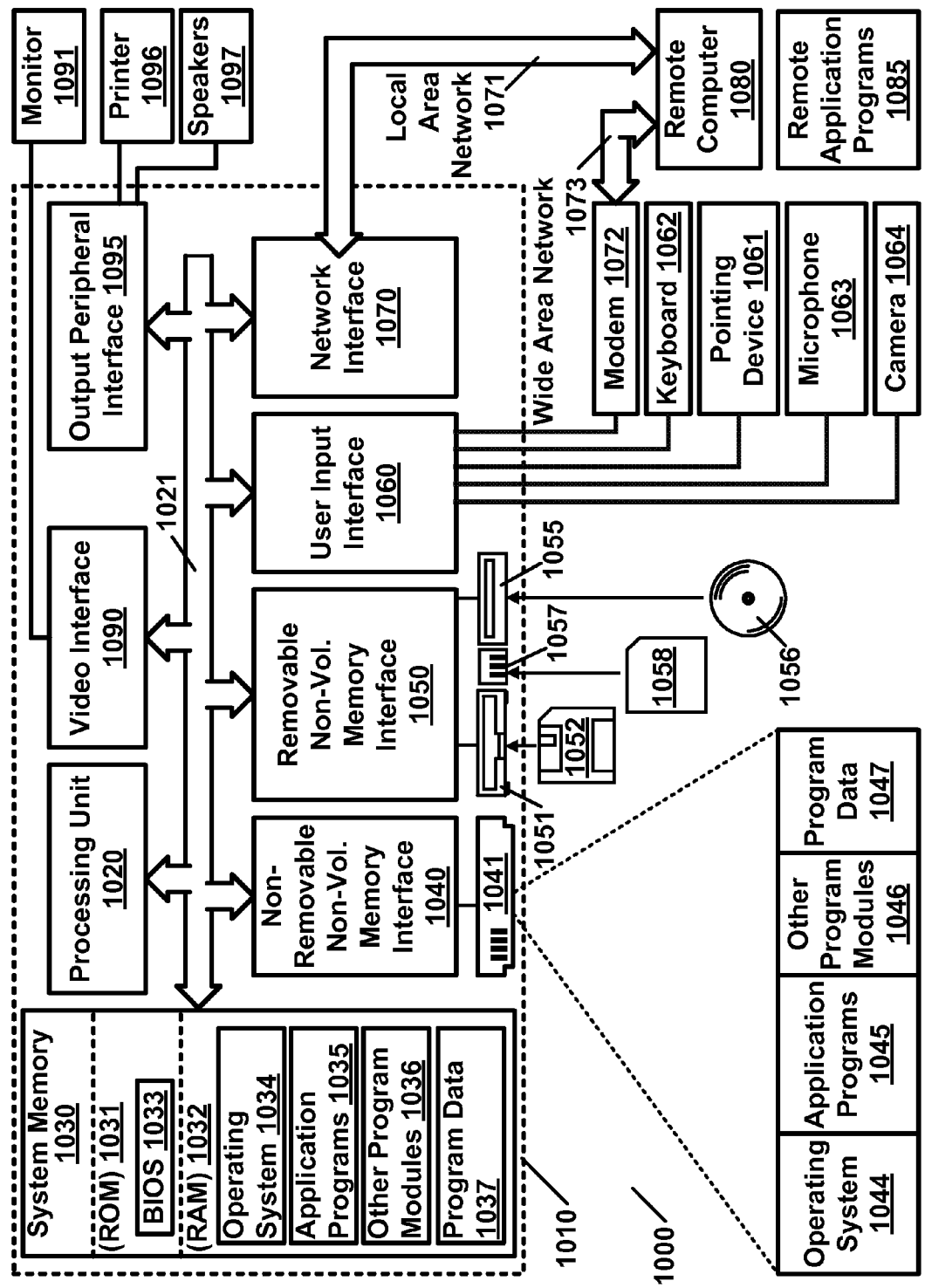
FIG. 10 is a block diagram of a computing environment that may be employed according to some aspects of an embodiment of the present invention.

FIG. 10 illustrates an example of a suitable computing system environment 1000 on which aspects of some embodiments may be implemented. The computing system environment 1000 is only one example of a suitable computing environment and is not intended to suggest any limitation as to the scope of use or functionality of the claimed subject matter. Neither should the computing environment 1000 be interpreted as having any dependency or requirement relating to any one or combination of components illustrated in the exemplary operating environment 1000.

Embodiments are operational with numerous other general purpose or special purpose computing system environments or configurations. Examples of well-known computing systems, environments, and/or configurations that may be suitable for use with various embodiments include, but are not limited to, embedded computing systems, personal computers, server computers, hand-held or laptop devices, multiprocessor systems, microprocessor-based systems, set top boxes, programmable consumer electronics, network PCs, minicomputers, mainframe computers, telephony systems, distributed computing environments that include any of the above systems or devices, and the like.

Embodiments may be described in the general context of computer-executable instructions, such as program modules, being executed by a computer. Generally, program modules include routines, programs, objects, components, data structures, etc. that perform particular tasks or implement particular abstract data types. Some embodiments are designed to be practiced in distributed computing environments where tasks are performed by remote processing devices that are linked through a communications network. In a distributed computing environment, program modules are located in both local and remote computer storage media including memory storage devices.

With reference to FIG. 10, an example system for implementing some embodiments includes a general-purpose computing device in the form of a computer 1010. Components of computer 1010 may include, but are not limited to, a processing unit 1020, a system memory 1030, and a system bus 1021 that couples various system components including the system memory to the processing unit 1020.

Computer 1010 typically includes a variety of computer readable media. Computer readable media can be any available media that can be accessed by computer 1010 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, random access memory (RAM), read-only memory (ROM), electrically erasable programmable read-only memory (EEPROM), flash memory or other memory technology, compact disc read-only memory (CD-ROM), digital versatile disks (DVD) or other optical disk storage, magnetic cassettes, magnetic tape, magnetic disk storage or other magnetic storage devices, or any other medium which can be used to store the desired information and which can be accessed by computer 1010. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of any of the above should also be included within the scope of computer readable media.

The system memory 1030 includes computer storage media in the form of volatile and/or nonvolatile memory such as ROM 1031 and RAM 1032. A basic input/output system 1033 (BIOS), containing the basic routines that help to transfer information between elements within computer 1010, such as during start-up, is typically stored in ROM 1031. RAM 1032 typically contains data and/or program modules that are immediately accessible to and/or presently being operated on by processing unit 1020. By way of example, and not limitation, FIG. 10 illustrates operating system 1034, application programs 1035, other program modules 1036, and program data 1037.

The computer 1010 may also include other removable/non-removable volatile/nonvolatile computer storage media. By way of example only, FIG. 10 illustrates a hard disk drive 1041 that reads from or writes to non-removable, nonvolatile magnetic media, a magnetic disk drive 1051 that reads from or writes to a removable, nonvolatile magnetic disk 1052, a flash drive reader 1057 that reads flash drive 1058, and an optical disk drive 1055 that reads from or writes to a removable, nonvolatile optical disk 1056 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 1041 is typically connected to the system bus 1021 through a non-removable memory interface such as interface 1040, and magnetic disk drive 1051 and optical disk drive 1055 are typically connected to the system bus 1021 by a removable memory interface, such as interface 1050.

The drives and their associated computer storage media discussed above and illustrated in FIG. 10, provide storage of computer readable instructions, data structures, program modules and other data for the computer 1010. In FIG. 10, for example, hard disk drive 1041 is illustrated as storing operating system 1044, application programs 1045, program data 1047, and other program modules 1046. Additionally, for example, non-volatile memory may include sensor signal processing modules, threshold excedent determination module(s), combinations thereof, and/or the like.

A user may enter commands and information into the computer 1010 through input devices such as a keyboard 1062, a microphone 1063, a camera 1064, and a pointing device 1061, such as a mouse, trackball or touch pad. These and other input devices are often connected to the processing unit 1020 through a user input interface 1060 that is coupled to the system bus, but may be connected by other interface and bus structures, such as a parallel port, a game port or a universal serial bus (USB). A monitor 1091 or other type of display device may also connected to the system bus 1021 via an interface, such as a video interface 1090. Other devices, such as, for example, speakers 1097 and printer 1096 may be connected to the system via peripheral interface 1095.

The computer 1010 is operated in a networked environment using logical connections to one or more remote computers, such as a remote computer 1080. The remote computer 1080 may be a personal computer, a hand-held device, a server, a router, a network PC, a peer device or other common network node, and typically includes many or all of the elements described above relative to the computer 1010. The logical connections depicted in FIG. 10 include a LAN 1071 and a WAN 1073, but may also include other networks. Such networking environments are commonplace in offices, enterprise-wide computer networks, intranets and the Internet.

When used in a LAN networking environment, the computer 1010 is connected to the LAN 1071 through a network interface or adapter 1070. When used in a WAN networking environment, the computer 1010 typically includes a modem 1072 or other means for establishing communications over the WAN 1073, such as the Internet. The modem 1072, which may be internal or external, may be connected to the system bus 1021 via the user input interface 1060, or other appropriate mechanism. The modem 1072 may be wired or wireless. Examples of wireless devices may comprise, but are limited to: Wi-Fi and Bluetooth. In a networked environment, program modules depicted relative to the computer 1010, or portions thereof, may be stored in the remote memory storage device. By way of example, and not limitation, FIG. 10 illustrates remote application programs 1085 as residing on remote computer 1080. It will be appreciated that the network connections shown are exemplary and other means of establishing a communications link between the computers may be used.

In this specification, "a" and "an" and similar phrases are to be interpreted as "at least one" and "one or more." References to "an" embodiment in this disclosure are not necessarily to the same embodiment.

Many of the elements described in the disclosed embodiments may be implemented as modules. A module is defined here as an isolatable element that performs a defined function and has a defined interface to other elements. The modules described in this disclosure may be implemented in hardware, a combination of hardware and software, firmware, wetware (i.e. hardware with a biological element) or a combination thereof, all of which are behaviorally equivalent. For example, modules may be implemented using computer hardware in combination with software routine(s) written in a computer language (such as C, C++, FORTRAN, Java, Basic, Matlab or the like) or a modeling/simulation program (such as Simulink, Stateflow, GNU Octave, or LabVIEW MathScript). Additionally, it may be possible to implement modules using physical hardware that incorporates discrete or programmable analog, digital and/or quantum hardware. Examples of programmable hardware include: computers, microcontrollers, microprocessors, application-specific integrated circuits (ASICs); field programmable gate arrays (FPGAs); and complex programmable logic devices (CPLDs). Computers, microcontrollers and microprocessors are programmed using languages such as assembly, C, C++ or the like. FPGAs, ASICs and CPLDs are often programmed using hardware description languages (HDL) such as VHSIC hardware description language (VHDL) or Verilog that configure connections between internal hardware modules with lesser functionality on a programmable device. Finally, it needs to be emphasized that the above mentioned technologies may be used in combination to achieve the result of a functional module.

The disclosure of this patent document incorporates material which is subject to copyright protection. The copyright owner has no objection to the facsimile reproduction by anyone of the patent document or the patent disclosure, as it appears in the Patent and Trademark Office patent file or records, for the limited purposes required by law, but otherwise reserves all copyright rights whatsoever.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments. In particular, it should be noted that, for example purposes, the above explanation has focused on the example(s) monitoring environmental quality in a medical facility. However, one skilled in the art will recognize that embodiments of the invention could be used to monitor environmental quality in other locations such a pharmaceutical manufacturing facility, a semiconductor manufacturing facility, a forensics laboratory, a house, a city, a cruise ship, and/or the like.

In addition, it should be understood that any figures that highlight any functionality and/or advantages, are presented for example purposes only. The disclosed architecture is sufficiently flexible and configurable, such that it may be utilized in ways other than those shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology to determine quickly from a cursory inspection the nature and essence of the technical disclosure of the application. The Abstract of the Disclosure is not intended to be limiting as to the scope in any way.

What is claimed is:

1. An apparatus comprising:
   a. a data bus;
   b. a multitude of sensors connected to the data bus, the multitude of sensors including:
      i. at least one particle counter; and
      ii. at least one differential pressure sensor;
   c. at least one processing unit connected to the data bus;

d. a communications interface connected to the data bus configured to communicate with at least one external monitoring device; and
e. a memory comprising:
 i. a data segment; and
 ii. a machine readable instructions segment, the computer readable instructions configured to cause the at least one processing unit to:
  1. collect sensor data from at least one of the multitude of sensors;
  2. generate processed sensor data from the sensor data; and
  3. set at least one alarm based, at least in part on processed sensor data, when at least one predetermined condition persists for a specified period of time.

2. The apparatus according to claim 1, wherein the machine readable instructions segment further include machine readable instructions configured to cause the at least one processing unit to set the at least one alarm when a predetermined threshold is exceeded.

3. The apparatus according to claim 1, wherein the machine readable instructions segment further include machine readable instructions configured to cause the at least one processing unit to set the at least one alarm when a sensor specific threshold is exceeded.

4. The apparatus according to claim 1, wherein the machine readable instructions segment further include machine readable instructions configured to cause the at least one processing unit to set the at least one alarm when a multitude of sensor thresholds are exceeded.

5. The apparatus according to claim 1, wherein the machine readable instructions segment further include machine readable instructions configured to cause the at least one processing unit to set the at least one alarm when an alarm threshold calculation involving a multitude of sensor thresholds is exceeded.

6. The apparatus according to claim 1, wherein the machine readable instructions segment further include machine readable instructions configured to cause the at least one processing unit to set the at least one alarm according to an alarm fatigue rule.

7. The apparatus according to claim 1, wherein the machine readable instructions segment further include machine readable instructions configured to cause the at least one processing unit to categorize at least one alarm as at least one of the following:
a. a data alarm;
b. a network alarm;
c. a calibration alarm; and
d. a combination of the above.

8. The apparatus according to claim 1, wherein the machine readable instructions segment further include machine readable instructions configured to cause the at least one processing unit to report at least one alarm to at least one of the following:
a. a facility worker;
b. a network administrator;
c. a healthcare professional;
d. a emergency responder; and
e. a combination of the above.

9. The apparatus according to claim 1, wherein the machine readable instructions segment further include machine readable instructions configured to cause the at least one processing unit to report at least one alarm according to an alarm notification list.

10. The apparatus according to claim 1, wherein the machine readable instructions segment further include machine readable instructions configured to cause the at least one processing unit to report at least one alarm after an alarm specific delay.

11. The apparatus according to claim 1, wherein the machine readable instructions segment further include machine readable instructions configured to cause the at least one processing unit to reset at least one alarm after an reset delay.

12. The apparatus according to claim 1, wherein the machine readable instructions segment further include machine readable instructions configured to cause the at least one processing unit to communicate at least one alarm to at least one external monitoring device.

13. The apparatus according to claim 1, wherein the machine readable instructions segment further include machine readable instructions configured to communicate an alarm to at least one other apparatus.

14. The apparatus according to claim 1, wherein the machine readable instructions segment further include machine readable instructions configured to cause the at least one processing unit to set the at least one alarm when at least one predetermined cleanroom standard value is exceeded.

15. The apparatus according to claim 1, wherein the machine readable instructions segment further include machine readable instructions configured to cause the at least one processing unit to set the at least one alarm when a combination of at least two predetermined cleanroom standards is exceeded.

16. The apparatus according to claim 1, wherein the machine readable instructions segment further include machine readable instructions configured to cause the at least one processing unit to set the at least one alarm when at least one predetermined facility guideline value is exceeded.

17. The apparatus according to claim 1, wherein the machine readable instructions segment further include machine readable instructions configured to cause the at least one processing unit to set the at least one alarm when a combination of at least two predetermined facility guideline values is exceeded.

18. The apparatus according to claim 1, wherein the machine readable instructions segment further include machine readable instructions configured to cause the at least one processing unit to set the at least one alarm when at least one predetermined ISO 9 value is exceeded.

19. The apparatus according to claim 1, wherein the multitude of sensors further comprises at least one of the following:
a. at least one light sensor;
b. at least one sound sensor;
c. at least one humidity sensor;
d. at least one temperature sensor;
e. at least one air quality sensor;
f. at least one at least one $CO_2$ sensor; and
g. at least one hazardous gas sensor.

20. The apparatus according to claim 1, wherein the at least one external monitoring device comprises at least one of the following:
a. at least one other apparatus;
b. at least one environmental monitoring device;
c. at least one environmental sensor device;
d. at least one SaaS;

e. at least one environmental monitoring program;
f. at least one cloud based server; and
g. at least one network server.

* * * * *